US011613462B2

(12) United States Patent
Lynn

(10) Patent No.: US 11,613,462 B2
(45) Date of Patent: *Mar. 28, 2023

(54) MULTIPLE TAP SYSTEM FOR GENERATING AND DISTRIBUTING AQUEOUS OZONE TO DIFFERENT PIECES OF EQUIPMENT

(71) Applicant: Daniel W. Lynn, Omaha, NE (US)

(72) Inventor: Daniel W. Lynn, Omaha, NE (US)

(*) Notice: Subject to any disclaimer, the term of this patent is extended or adjusted under 35 U.S.C. 154(b) by 96 days.

This patent is subject to a terminal disclaimer.

(21) Appl. No.: 17/391,152

(22) Filed: Aug. 2, 2021

(65) Prior Publication Data
US 2021/0354985 A1  Nov. 18, 2021

Related U.S. Application Data

(63) Continuation-in-part of application No. 17/150,424, filed on Jan. 15, 2021, now Pat. No. 11,078,078, and
(Continued)

(51) Int. Cl.
*C02F 1/78* (2023.01)
*A61L 2/18* (2006.01)
(Continued)

(52) U.S. Cl.
CPC .............. *C01B 13/11* (2013.01); *A61L 2/183* (2013.01); *B01F 23/2323* (2022.01); *B01F 25/31242* (2022.01); *C02F 1/78* (2013.01); *C11D 3/48* (2013.01); *C11D 7/04* (2013.01); *C11D 11/0023* (2013.01); *C11D 11/0064* (2013.01);
(Continued)

(58) Field of Classification Search
CPC ...... C01B 13/11; A61L 2/183; A61L 2202/11; B01F 23/2323; B01F 25/31242; B01F 23/237613; B01F 23/2373; B01F 25/3121; B01F 25/42; B01F 33/813; C02F 1/78; C02F 2201/782; C02F 2209/04; C02F 2209/40; C02F 2303/04; C02F 2209/03;
(Continued)

(56) References Cited

U.S. PATENT DOCUMENTS 1,363,589 A  12/1920  Hartman
6,030,586 A   2/2000  Kuan
(Continued)

*Primary Examiner* — Hayden Brewster
(74) *Attorney, Agent, or Firm* — Nasr Patent Law LLC; Faisal K. Abou-Nasr

(57) ABSTRACT

A system for creating an oxidation reduction potential (ORP) in water employs a plurality of ozone supply units housed in separate enclosures. The ozone supply units feed into a manifold that contains a plurality of fluid paths and has one or more ozone intake ports. The ozone intake ports are fluidically coupled to one or more ozone output ports of each ozone supply unit. The manifold includes a plurality of flow switches configured to transmit control signals to one or more controllers of each ozone supply unit in response to sensing a flow of water through the fluid paths in order to cause the ozone supply units to generate ozone. The manifold also includes a plurality of fluid mixers that are fluidically coupled to the ozone intake ports and configured to introduce the ozone generated by the ozone supply units into the water flowing through the fluid paths.

10 Claims, 10 Drawing Sheets

Related U.S. Application Data a continuation-in-part of application No. 17/150,449, filed on Jan. 15, 2021, now Pat. No. 11,078,079, said application No. 17/150,424 is a continuation-in-part of application No. 17/078,799, filed on Oct. 23, 2020, now Pat. No. 11,305,991, which is a continuation of application No. 15/476,326, filed on Mar. 31, 2017, now abandoned, which is a continuation-in-part of application No. 15/446,331, filed on Mar. 1, 2017, now Pat. No. 10,232,070, which is a continuation-in-part of application No. 15/355,884, filed on Nov. 18, 2016, now abandoned, which is a continuation-in-part of application No. 15/050,777, filed on Feb. 23, 2016, now abandoned.

(60) Provisional application No. 62/121,770, filed on Feb. 27, 2015.

(51) Int. Cl.
| | | |
|---|---|---|
| *C11D 7/04* | (2006.01) | |
| *B01F 23/232* | (2022.01) | |
| *C01B 13/11* | (2006.01) | |
| *C11D 3/48* | (2006.01) | |
| *C11D 11/00* | (2006.01) | |
| *B01F 25/312* | (2022.01) | |
| *B01F 23/237* | (2022.01) | |

(52) U.S. Cl.
CPC ... *A61L 2202/11* (2013.01); *B01F 23/237613* (2022.01); *C02F 2201/782* (2013.01); *C02F 2209/04* (2013.01); *C02F 2209/40* (2013.01); *C02F 2303/04* (2013.01)

(58) Field of Classification Search
CPC .. C02F 1/008; C11D 3/48; C11D 7/04; C11D 11/0023; C11D 11/0064
USPC ...... 204/157.5; 210/5, 87, 90, 96.1, 97, 136, 210/137, 150, 151, 192, 202, 259, 607, 210/614, 631, 724, 739, 741, 743, 746, 210/750, 760, 769
See application file for complete search history.

(56) References Cited

U.S. PATENT DOCUMENTS

| | | |
|---|---|---|
| 6,153,105 A | 11/2000 | Tadlock et al. |
| 6,334,328 B1 | 1/2002 | Brill |
| 6,685,825 B1 | 2/2004 | Chang |
| 8,071,526 B2 | 12/2011 | Lynn |
| 8,075,705 B2 | 12/2011 | Lynn |
| 9,068,149 B2 | 6/2015 | Lynn |
| 9,151,528 B2 | 10/2015 | Erbs et al. |
| 9,174,845 B2 | 11/2015 | Lynn |
| 9,522,348 B2 | 12/2016 | Lynn |
| 11,078,078 B2 * | 8/2021 | Lynn ................... C11D 11/0064 |
| 11,078,079 B2 * | 8/2021 | Lynn ................... C11D 11/0064 |
| 2003/0156978 A1 | 8/2003 | Gillette |
| 2004/0004042 A1 | 1/2004 | Hadley et al. |
| 2004/0168989 A1 | 9/2004 | Tempest |
| 2009/0142225 A1 | 6/2009 | Tornqvist |
| 2009/0185959 A1 | 7/2009 | Weber et al. |
| 2010/0219137 A1 | 9/2010 | Lacasse |
| 2013/0193081 A1 | 8/2013 | Vasiliu et al. |
| 2013/0195725 A1 | 8/2013 | Lynn |
| 2013/0341285 A1 | 12/2013 | Marion |
| 2014/0027388 A1 | 1/2014 | Constant |
| 2014/0263097 A1 | 9/2014 | Lynn |
| 2016/0251243 A1 | 9/2016 | Lynn |
| 2017/0209609 A1 | 7/2017 | Lynn |

* cited by examiner

MULTIPLE TAP SYSTEM FOR GENERATING AND DISTRIBUTING AQUEOUS OZONE TO DIFFERENT PIECES OF EQUIPMENT

CROSS-REFERENCE TO RELATED APPLICATIONS

The present application is a Continuation-in-Part of U.S. application Ser. No. 17/150,424 filed Jan. 15, 2021 entitled MULTI-UNIT SYSTEM FOR CREATING AN OXIDATION REDUCTION POTENTIAL (ORP) IN WATER WITH MULTI-PATH MANIFOLD FOR MIXING AND DISTRIBUTION which is a Continuation-in-Part of U.S. application Ser. No. 17/078,799 filed Oct. 23, 2020 entitled SYSTEMS AND METHODS FOR CREATING AN OXIDATION REDUCTION POTENTIAL (ORP) IN WATER FOR PATHOGENIC CONTROL WITH THE WATER AND OZONE SOLUTIONS THEREOF BEING SUPPLIED TO ONE OR MORE WASH-DOWN STATIONS which is a Continuation of U.S. application Ser. No. 15/476,326 filed Mar. 31, 2017 entitled SYSTEMS AND METHODS FOR CREATING AN OXIDATION REDUCTION POTENTIAL (ORP) IN WATER FOR PATHOGENIC CONTROL WITH THE WATER AND OZONE SOLUTIONS THEREOF BEING SUPPLIED TO ONE OR MORE WASH-DOWN STATIONS which is a Continuation-in-Part of U.S. application Ser. No. 15/446,331 filed Mar. 1, 2017 entitled SYSTEMS AND METHODS FOR CREATING AN OXIDATION REDUCTION POTENTIAL (ORP) IN WATER FOR PATHOGENIC CONTROL WITH THE WATER AND OZONE SOLUTIONS THEREOF BEING SUPPLIED TO ONE OR MORE WASH-DOWN STATIONS which is a Continuation-in-Part of U.S. application Ser. No. 15/355,884 filed Nov. 18, 2016 entitled SYSTEMS AND METHODS FOR CREATING AN OXIDATION REDUCTION POTENTIAL (ORP) IN WATER FOR PATHOGENIC CONTROL which is a Continuation-in-Part of U.S. application Ser. No. 15/050,777 filed Feb. 23, 2016 entitled SYSTEMS AND METHODS FOR CREATING AN OXIDATION REDUCTION POTENTIAL (ORP) IN WATER FOR PATHOGENIC CONTROL which claims the benefit of U.S. Provisional Application Ser. No. 62/121,770 filed Feb. 27, 2015 entitled SYSTEMS AND METHODS FOR CREATING AN OXIDATION REDUCTION POTENTIAL (ORP) IN WATER FOR PATHOGENIC CONTROL, all of which are incorporated by reference. The present application is also a Continuation-in-Part of U.S. application Ser. No. 17/150,449 filed Jan. 15, 2021 entitled SYSTEM FOR CREATING AN OXIDATION REDUCTION POTENTIAL (ORP) IN WATER WITH MULTI-PATH MANIFOLD FOR MIXING AND DISTRIBUTION, which is incorporated by reference.

TECHNICAL FIELD

The present disclosure relates to systems for creating an oxidation reduction potential (ORP) in water for pathogenic control, and more particularly, to a multi-unit system that employs a multi-path manifold to mix and distribute water and ozone solution.

BACKGROUND

Water intended for potable use (e.g., drinking water), may contain disease-causing organisms, or pathogens, which can originate from the source of the water, from resistance to water treatment techniques, from improper or ineffectual water treatment techniques, or so forth. Pathogens include various types of bacteria, viruses, protozoan parasites, and other organisms. To protect drinking water from disease-causing organisms, or pathogens, water suppliers often add a disinfectant, such as chlorine, to the water. However, disinfection practices can be ineffectual because certain microbial pathogens, such as *Cryptosporidium*, are highly resistant to traditional disinfection practices. Also, disinfectants themselves can react with naturally-occurring materials in the water to form byproducts, such as trihalomethanes and haloacetic acids, which may pose health risks.

A major challenge for water suppliers is how to control and limit the risks from pathogens and disinfection byproducts. It is important to provide protection from pathogens while simultaneously minimizing health risks to the population from disinfection byproducts. Oxidation reduction potential (ORP) can be used for water system monitoring to reflect the antimicrobial potential of the water, without regard to the water quality, with the benefit of a single-value measure of the disinfection potential, showing the activity of the disinfectant rather than the applied dose.

There are a number of systems that generate ORP in water by injecting ozone into the water to create an ozone and water solution. However, high pressure water applications present challenges, often requiring the use of an intermediate tank that must be filled prior to use (much like a water heater). To overcome such challenges, there is a need for improvements in the mixing and distribution of water and ozone solution.

SUMMARY

Aspects of this disclosure are directed to a multi-unit system for creating an oxidation reduction potential (ORP) in water using a multi-path manifold to mix and distribute water and ozone solution. In embodiments, the system includes a plurality of ozone supply units and a manifold.

Each ozone supply unit includes an enclosure having one or more air intake ports and one or more ozone output ports. A plurality of ozone generators are disposed within the supply unit enclosure. The plurality of ozone generates are fluidically coupled to the one or more air intake ports and the one or more ozone output ports of the supply unit enclosure. One or more controllers are also disposed within the supply unit enclosure. The one or more controllers are communicatively coupled to the plurality of ozone generators.

The manifold includes a manifold enclosure containing a plurality of fluid paths and having one or more ozone intake ports. The one or more ozone intake ports are fluidically coupled to the one or more ozone output ports of the supply unit enclosure of each ozone supply unit. A plurality of flow switches are disposed within the manifold enclosure. The plurality of flow switches are configured to transmit one or more control signals to the one or more controllers of each ozone supply unit in response to sensing a flow of water through the plurality of fluid paths. The one or more controllers are configured to cause the plurality of ozone generators of each ozone supply unit to generate ozone in response to the one or more control signals. A plurality of fluid mixers are also disposed within the manifold enclosure. The plurality of fluid mixers are fluidically coupled to the one or more ozone intake ports and are configured to introduce the ozone generated by the plurality of ozone generators into the water flowing through the plurality of fluid paths.

In embodiments, the supply unit enclosure of each ozone supply unit and the manifold enclosure are independently locatable, separate structures. The supply unit enclosure of each ozone supply unit and the manifold enclosure may be fluidically coupled, e.g., by one or more tubes for transferring ozone from the supply unit enclosure of each ozone supply unit to the manifold enclosure. The supply unit enclosure of each ozone supply unit and the manifold enclosure may also be communicatively coupled, e.g., by one or more connectors for transmitting signals between the supply unit enclosure of each ozone supply unit and the manifold enclosure.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

Figure 1A:
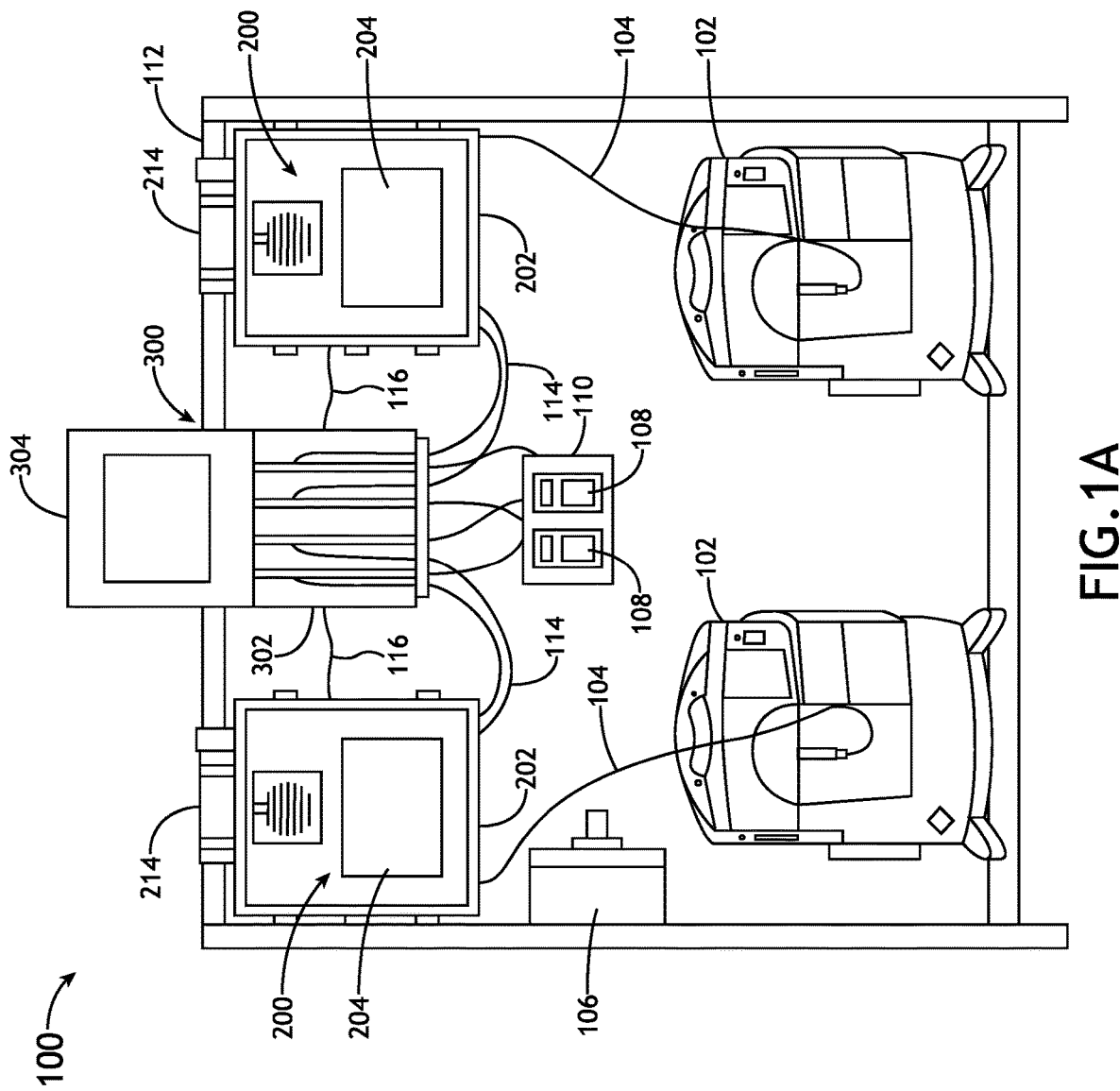
FIG. 1A is a front view of system for distributing ozonated fluid, in accordance with one or more embodiments of this disclosure.

Reference will now be made in detail to the subject matter disclosed, which is illustrated in the accompanying drawings.

Embodiments of this disclosure are directed to a system for distributing ozonated fluid using a multi-path manifold to mix and distribute water and ozone solution. The system can be used for cleansing and/or degreasing hard surfaces such as plastic, glass, ceramic, porcelain, stainless steel, or the like. The system can also be used for cleansing and/or degreasing equipment such as food service equipment which may include, but are not limited to, ovens, ranges, fryers, grills, steam cookers, oven stacks, refrigerators, coolers, holding cabinets, cold food tables, worktables, ice machines, faucets, beverage dispensing equipment, beer dispensers, shelving food displays, dish washing equipment, and grease traps. The system can also be used for cleansing and/or degreasing HVAC or plumbing systems such as roof top units, air scrubbers, humidifiers, water heaters, pumps, or the like. The system can also be used for commercial/industrial equipment including, but not limited to, washdown stations (e.g., as described in U.S. Pat. No. 10,232,070), wall washing systems (e.g., as described in U.S. Pat. No. 10,232,071), vegetable and fruit washers (e.g., as described in U.S. Pat. No. 10,238,125), potato washers (e.g., as described in U.S. Pat. No. 10,231,466), carcass/subprimal cleaning systems, wastewater treatment systems, air scrubbers, laundry washing machines (e.g., as described in U.S. Pat. Nos. 10,233,583 and 10,233,584), and water softeners.

An ORP value can be used for water system monitoring to reflect the antimicrobial potential of a given sample of water. ORP is measured in millivolts (mV), with typically no correction for solution temperature, where a positive voltage shows a solution attracting electrons (e.g., an oxidizing agent). For instance, chlorinated water will show a positive ORP value whereas sodium sulfite (a reducing agent) loses electrons and will show a negative ORP value. Similar to pH, ORP is not a measurement of concentration directly, but rather of activity level. In a solution of only one active component, ORP indicates concentration. The World Health Organization (WHO) adopted an ORP standard for drinking water disinfection of 650 millivolts. That is, the WHO stated that when the oxidation-reduction potential in a body of water measures 650 (about ⅔ of a volt), the sanitizer in the water is active enough to destroy harmful organisms almost instantaneously. For example, *E. coli, Salmonella, Listeria*, and Staph pathogens have survival times of under 30 seconds when the ORP is above 650 mV, compared against >300 seconds when it is below 485 mV.

An example ORP sensor uses a small platinum surface to accumulate charge without reacting chemically. That charge is measured relative to the solution, so the solution "ground" voltage comes from the reference junction. For example, an ORP probe can be considered a millivolt meter, measuring the voltage across a circuit formed by a reference electrode constructed of silver wire (in effect, the negative pole of the circuit), and a measuring electrode constructed of a platinum band (the positive pole), with the water in-between.

Increasingly, microbial issues are commanding the attention of water treatment operators, regulators, media, and consumers. There are many treatment options to eliminate pathogenic microbes from drinking water. One such option includes ozone (03), an oxidizing agent approved for drinking water treatment by the U.S. Environmental Protection Agency. For instance, ozone is one of the strongest disinfectants approved for potable water treatment capable of inactivating bacteria, viruses, *Giardia*, and *Cryptosporidium*.

The disclosed system may be configured to output water having an ORP of about 600 mV to about 1000 mV, with particular embodiments being configured to output water having an ORP of about 900 mV to provide pathogenic control. Additionally, the system may be configured to reduce the surface tension of the water being used to cleanse and/or degrease hard surfaces and equipment by creating a water and ozone solution wherein the surface tension of the water is reduced from about 72 Millinewtons per meter at 20 degrees Centigrade to about 48-58 Millinewtons per meter at 20 degrees Centigrade to greatly improve the cleansing and/or degreasing qualities thereof.

In embodiments, the system employs a multi-path manifold to mix and distribute water and ozone solution. Through the use of fluid mixing and distribution paths contained within a manifold enclosure that is structurally separate from an ozone supply unit, the system is able to handle high pressure water flow through the manifold without fear of a leak causing damage to electronic components associated with the ozone supply unit (e.g., ozone generators, controllers, relays, etc.). Furthermore, the fluid paths may be linearly disposed within the manifold enclosure for improved throughput with a reduced footprint.

FIGS. 1A through 3 illustrate a system 100 for distributing ozonated fluid, in accordance with one or more embodiments of this disclosure. In embodiments, the system 100 includes a plurality of ozone supply units 200 (e.g., two or more ozone supply units 200) configured to output ozone and a manifold 300 to mix the ozone into the water and to distribute a resulting water and ozone solution. Although the system 100 is discussed with regard to applications that employ water to generate a water and ozone solution, it is contemplated that the system 100 may be configured to generate other types of ozonated fluid solutions for the purposes of cleansing, degreasing, decontaminating, and/or fluid treatment.

As shown in FIG. 1A, the ozone supply units 200 and the manifold 300 may include respective enclosures (i.e., supply unit enclosures 202 and manifold enclosure 302). In embodiments, the supply unit enclosures 202 and the manifold enclosure 302 are independently locatable, separate structures. While the supply unit enclosures 202 and the manifold enclosure 302 are separate and capable of being disposed at a distance from one another, the supply unit enclosures 202 and the manifold enclosure 302 are still fluidically coupled by one or more tubes 114 (e.g., flexible tubing, pipes, etc.) for transferring ozone from the ozone supply unit 200 to the manifold 300. The supply unit enclosure 202 and the manifold enclosure 302 may also be communicatively coupled by one or more connectors 116 (e.g., wires, cables, optical fibers, etc.) for transmitting signals between the ozone supply unit 200 and the manifold 300. In other embodiments, the ozone supply unit 200 and the manifold 300 may include wireless communication interfaces (e.g., wireless receivers, transmitters, and/or transceivers) for sending signals from one device to the other.

Each supply unit enclosure 202 may have a securable lid/cover 204 that can enclose (e.g., when secured/closed) and provide access to (e.g., when removed/opened) the components housed in an interior portion of the supply unit enclosure 202. In some embodiments, the securable lid/cover 204 may be secured to the supply unit enclosure 202 by a hinge on one side and a latch or fastener on an opposing side. In other embodiments, the securable lid/cover 204 may be a sliding cover or may be secured to the supply unit enclosure 202 by one or more fasteners (e.g., screws to mate with bores in the supply unit enclosure 202, latches, interference fit fasteners, clipping fasteners, magnetic fasteners, or the like). Each supply unit enclosure 202 may further include coupling portions to couple with a power source, a switch to engage or disengage power to the ozone supply unit 200/system 100, an indicator (e.g., a light source), any combination thereof, and so forth.

The manifold enclosure 302 may also have a securable lid/cover 304 that can enclose (e.g., when secured/closed) and provide access to (e.g., when removed/opened) the components housed in an interior portion of the manifold enclosure 302. In some embodiments, the securable lid/cover 304 may be a sliding cover or may be secured to the manifold enclosure 302 by one or more fasteners (e.g., screws to mate with bores in the manifold enclosure 302, latches, interference fit fasteners, clipping fasteners, magnetic fasteners, or the like). In other embodiments, the securable lid/cover 304 is secured to the manifold enclosure 302 by a hinge on one side and latch or fastener on an opposing side.

Figure 2:
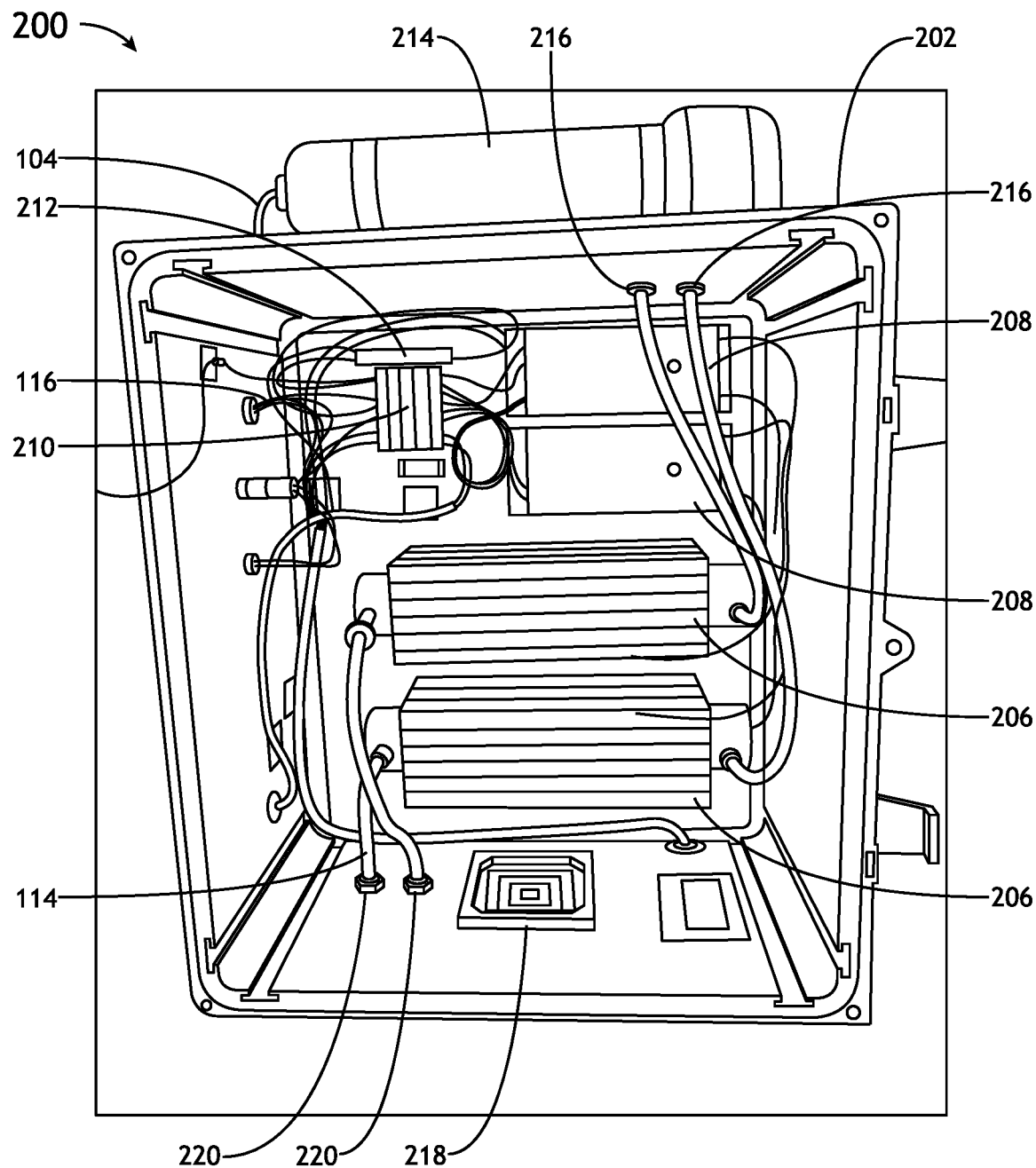
FIG. 2 is a perspective view of an open ozone supply unit of the system illustrated in FIGS. 1A and 1B, in accordance with one or more embodiments of this disclosure.

FIG. 2 illustrates an ozone supply unit 200 with the lid/cover 204 removed from the supply unit enclosure 202, in accordance with one or more embodiments of this disclosure. As shown in FIG. 2, the supply unit enclosure 202 includes one or more air intake ports 216 and one or more ozone output ports 220. The ozone supply unit 200 includes a plurality of ozone generators 206 (e.g., two or more generators 206) disposed within the supply unit enclosure 202. The ozone generators 206 are fluidically coupled to the one or more air intake ports 216 and the one or more ozone output ports 220 of the supply unit enclosure 202. One or more controllers 208 are also disposed within the supply unit enclosure 202. The one or more controllers 208 are communicatively coupled to the ozone generators 206.

In embodiments, each of the ozone generators 206 may include a corona discharge tube configured to use oxygen supplied via the one or more air intake ports 216 to generate ozone, such as through splitting of oxygen molecules in the air through electrical discharge caused by supplying power to a dielectric material within the corona discharge tube. For example, each ozone generator 206 may include an input port that is fluidically coupled to an air intake port 216 and configured to convert oxygen from incoming air into ozone. The ozone generators 206 may be powered by a power source 212 (e.g., a 120V/240V power supply). A power signal from power source 212 may be transformed via a transformer suitable for applying the voltage to the dielectric within the corona discharge tube of the ozone generator 206. For example, a transformer may be coupled to or integrated within a controller 208 for the ozone generator 206.

In some embodiments, the ozone generators 206 may be operated at 110 volts/60 Hz and have an operating frequency of about 450 KHz and 550 KHz, with a power rating of less than about 15 watts, and with a unit performance for electrical consumption of about 32 watts. For example, the ozone generators 206 may have an operating frequency of about 480 KHz. Further, the ozone generators 206 can be provided according to ISO 9001 CE standards.

Each of the ozone generators 206 may be configured to produce from about 800 mg ozone per hour to about 1200 mg ozone per hour, although other ranges may be appropriate depending on the application. In some embodiments, each of the ozone generators 206 produces about 1000 mg ozone per hour. The ozone generators 206 may include other methods and systems for generating ozone, including but not limited to, electrochemical cells configured to generate ozone from water by placing an anode and a cathode in contact with opposite sides of a proton exchange membrane (PEM), and supplying power to the cell, whereby water flowing over the surface of the anode breaks down into hydrogen atoms and oxygen atoms that assemble to form $O_3$ (ozone).

In embodiments, each ozone supply unit 200 may further include an air dryer 214 (or filter), which may be externally coupled to the supply unit enclosure 202. The air dryer 214 is configured to remove moisture from air before the air is supplied to the ozone generators 206 through the one or more air intake ports 216. The air dryer 214 may be configured to dry the air to a minus dew point by removing water vapor or moisture therefrom, where the water could inhibit the production of ozone by the ozone generators 206.

In some embodiments, the air dryer 214 includes or is coupled to an air compressor. The pressure provided by the compressor can vary depending on the water pressure supplied to the system 100, where the pressure applied by the compressor can be balanced based on the flow rate of air received by the ozone generators 206 via the one or more air intake ports 216 and the water pressure supplied to the system 100 to obtain a particular ORP of the water. For example, the compressor may be configured to compress the filtered air at least about 15 KPa (e.g., more particularly at a pressure of 18 KPa or about 2.6 psi) to provide a gas throughput in each ozone generator 206 of about 8 SCFH (standard cubic feet per hour), where the water pressure in each fluid path is about 25 psi to 100 psi (e.g., a reasonable rating for many residential and commercial facilities), to provide an ORP in the water at the water outlet of at least about 600 mV (e.g., about 600 mV to about 1000 mV, more particularly about 900 mV). At these pressures, each ozone generators 206 has a residence time of the gas of about three seconds. The pressure applied by the compressor can affect the rate at which the gas flows through an ozone generator 206, which can affect contact time of the air with the components of the ozone generator 206, which can also affect mass gas transfer rates within the ozone generator 206.

In embodiments, the ozone supply unit 200 includes a plurality of ozone generators 206. For example, in an embodiment illustrated FIG. 2, the ozone supply unit 200 includes two ozone generators 206. Each ozone generator 206 may be coupled to a respective air intake port 216 and ozone output port 220. However, in some embodiments, two or more ozone generators 206 may be fluidically connected in parallel between an air intake port 216 and an ozone output port 220. For example, splitters/combiners 218 can be used to fluidically couple each pair/set of ozone generators 206 in parallel. The ozone supply unit 200 may additionally/alternatively include two or more ozone generators 206 connected in series with one other. Such configurations provide one or more backup ozone generators 206 in case of malfunction or inoperability of one or more of the other ozone generators 206. On average, each ozone generator 206 may have an operating life of about 10,000 working hours.

In some embodiments, the supply unit enclosure 202 also includes a vent 218 (e.g., an exhaust vent) to bring cool air into the supply unit enclosure 202 and/or remove hot air from the supply unit enclosure 202. The vent 218 may be equipped with a fan to further facilitate airflow.

Although FIG. 2 illustrates one ozone supply unit 200, it is understood that other ozone supply units 200 in the system 100 may be identically or similarly structured. In this regard, any components or configurations described with regard to the ozone supply unit 200 in FIG. 2 are applicable to all of the ozone supply units 200 in the system 100.

Figure 3:
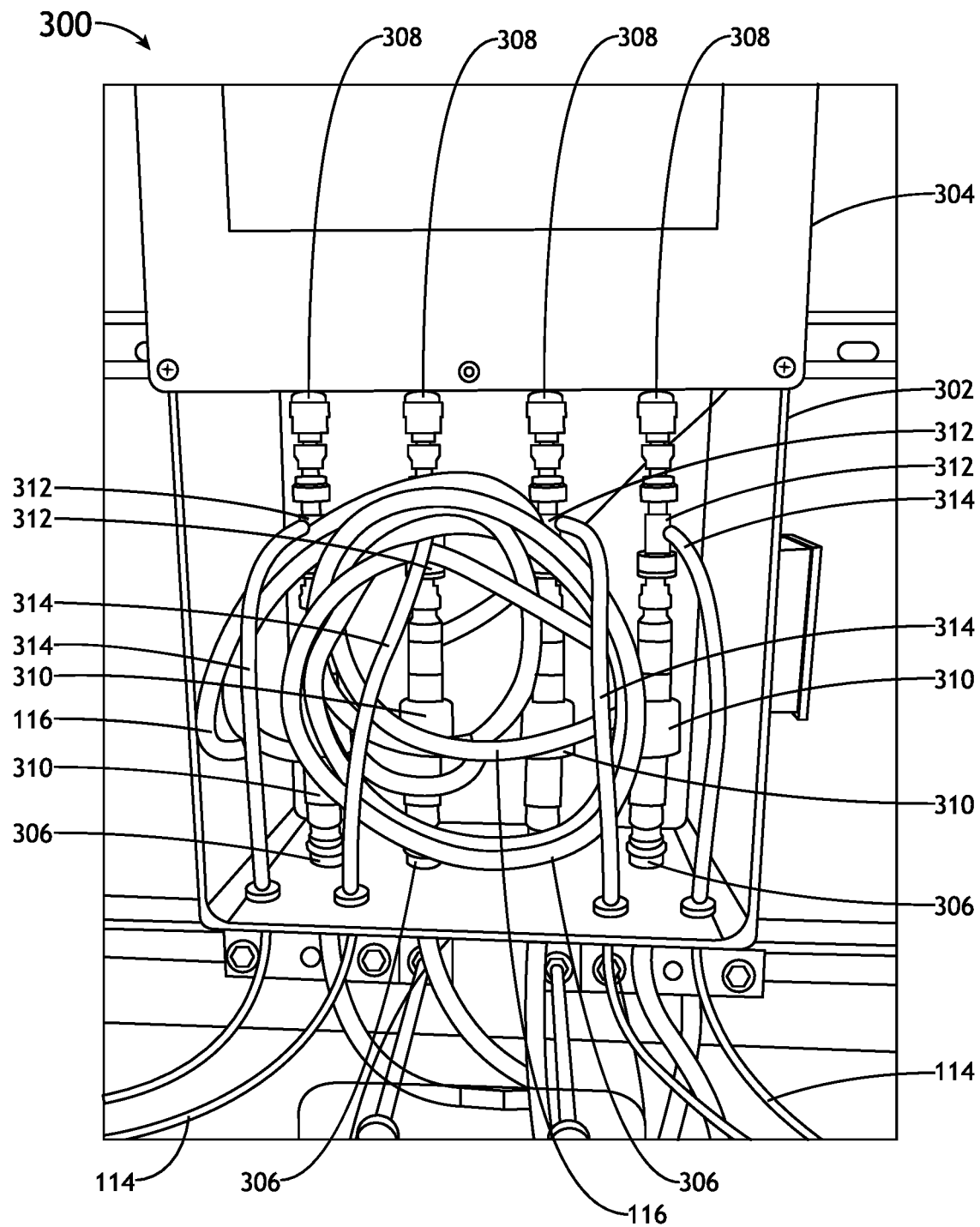
FIG. 3 is a perspective view of an open manifold of the system illustrated in FIGS. 1A and 1B, in accordance with one or more embodiments of this disclosure.

FIG. 3 illustrates the manifold 300 with the lid/cover 304 removed from the manifold enclosure 302, in accordance with one or more embodiments of this disclosure. As shown in FIG. 3, the manifold enclosure 302 contains a plurality of fluid paths. Each fluid path is defined between a respective water input port 306 and water output port 308. For example, in an embodiment illustrated in FIG. 3, the manifold 300 includes four fluid paths: a first fluid path extending linearly from first water input port 306 to a first water output port 308; a second fluid path extending linearly from second water input port 306 to a second water output port 308; a third fluid path extending linearly from a third water input port 306 to a third water output port 308; and a fourth fluid path extending linearly from a fourth water input port 306 to a fourth water output port 308. In embodiments, the enclosure 302 includes respective openings for the water input ports 306 and the water output ports 308. Furthermore, the water input ports 306 and the water output ports 308 may be located on opposite sides of the manifold enclosure 302, directly across from each other, so that the fluid paths run linearly from one side of the manifold enclosure 302 to the side of the manifold enclosure 302.

The manifold enclosure 302 further includes one or more ozone intake ports connected to ozone input tubes 314. The one or more ozone intake ports are fluidically coupled to the one or more ozone output ports 220 of the supply unit enclosure 202. In embodiments, one or more ozone intake ports of the manifold 300 are fluidically coupled to the one or more ozone output ports 220 of the ozone supply unit 200 by one or more tubes 114 (e.g., flexible tubing, pipes, etc.) for transferring ozone from the ozone supply units 200 to the manifold 300. In an embodiment illustrated in FIGS. 1A through 3, a first ozone supply unit 200 is fluidically coupled to the manifold 300 by one or more tubes 114 for transferring ozone from the first ozone supply unit 200 to the manifold 300, and a second ozone supply unit 200 is fluidically coupled to the manifold 300 by one or more tubes 114 for transferring ozone from the second ozone supply unit 200 to the manifold 300.

In embodiments, the manifold 300 includes one or more flow switches 310 (or meters) configured to sense a flow of water through the fluid paths. In some embodiments, the manifold includes a plurality of flow switches 310 disposed within the manifold enclosure 302. For example, each fluid path may include a respective flow switch 310 for sensing a flow of water through the fluid path.

Each flow switch 310 may be coupled between a respective water input port 306 and a respective water output port 308. In the embodiment illustrated in FIG. 3, the flow switches 310 are shown as being coupled between the water input ports 306 and fluid mixers 312; however, in other embodiments, the flow switches 310 could be coupled between the fluid mixers 312 and the water output ports 308. The flow switches 310 can be configured to provide electric signals indicative of water flow through the fluid paths. For example, the flow switches 310 may include mechanical flow switches/sensors, electromagnetic flow switches/sensors, pressure-based flow switches/sensors, optical flow switches/sensors, or the like, configured to provide an electric signal indicative of a flow of fluid (e.g., water) through the manifold 300. In some embodiments, the flow switches 310 may include solenoid-based flow switches/sensors, such as to avoid significant restriction of flow between the water input ports 306 and the water output ports 308.

In embodiments, the flow switches 310 are configured to transmit one or more control signals to the one or more controllers 208 in response to sensing a flow of water through the fluid paths. In response to receiving the one or more control signals, the one or more controllers 208 are configured to cause the ozone generators 206 to generate ozone. In some embodiments, the controllers 208 are transformers that become activated by control signals (e.g., status/power signals) transmitted by the flow switches 310 in response to sensing a flow of water through the fluid paths. In other embodiments, the controllers 208 may further include microprocessors, microcontrollers, or other programmable logic devices. In such embodiments, the one or more controllers 208 may be configured (e.g., programmed) to activate the transformers and/or ozone generators 206 in response to the control signals (e.g., status signals) and possibly based on other sensor signals being monitored by the one or more controllers 208.

The flow switches 310 may be communicatively coupled to the one or more controllers 208 by one or more connectors 116 (e.g., wires, cables, optical fibers, etc.) for transmitting signals between the ozone supply unit 200 and the manifold 300. In an embodiment illustrated in FIGS. 1A through 3, a first ozone supply unit 200 is communicatively coupled to the manifold 300 by one or more connectors 116 for transmitting signals between the first ozone supply unit 200 and the manifold 300, and a second ozone supply unit 200 is communicatively coupled to the manifold 300 by one or more connectors 116 for transmitting signals between the second ozone supply unit 200 and the manifold 300. As shown in FIG. 2, each ozone supply unit 200 may include a relay 210 that distributes the incoming signals to the one or more controllers 208. In other embodiments, the ozone supply unit 200 and the manifold 300 may include wireless communication interfaces (e.g., wireless receivers, transmitters, and/or transceivers) for sending signals from one device to the other.

In some embodiments, each fluid path includes a flow switch 310 that controls a respective ozone generator 206. For example, a first flow switch 310 may control a first ozone generator 206, a second flow switch 310 may control a second ozone generator 206, and so forth. In this regard, each fluid path may be capable of operating independently within the system 100. Alternatively, the flow switches 310 can work together to control the ozone generators 206. In this regard, the system 100 may only require one flow switch 310 connected to any of the fluid paths, or if the system 100 includes multiple flow switches 310, the flow switches 310 may provide redundancy and/or status indications for each of the fluid paths in order to detect faults (e.g., a faulty sensor, a clogged or disconnected fluid path, or the like). In some embodiments, a particular ozone generator 206 or all of the ozone generators 206 may be shut off when a fault is detected. For example, when a fault is detected in one fluid path, the ozone generator 206 for the faulty fluid path may be shut off, or alternatively, all of the ozone generators 206 may be shut off. Hybrid configurations are also contemplated. For example, two or more sets of flow switches 310 and ozone generators 206 may be assigned to a "zone" including two or more fluid paths, where the flow switches 310 are configured to work together to control the corresponding ozone generators 206 in each zone.

The manifold 300 further includes a plurality of fluid mixers 312 disposed within the manifold enclosure 302. As shown in FIG. 3, each fluid path may include a respective fluid mixer 312 configured to introduce/inject ozone generated by the ozone generators 206 into the water flowing through the fluid paths. For example, each fluid mixer 312 may be fluidically coupled to an ozone intake port and configured to inject at least a portion of the ozone received via the ozone intake port into the water flowing through the fluid paths. In some embodiments, each fluid mixer is connected to a respective ozone intake port by a respective ozone input tube 314. Alternatively, two or more fluid mixers 312 may be connected to a shared ozone intake port (e.g., by one or more ozone input tubes 314, using one or more T or Y connectors).

In embodiments, the fluid mixers 312 may be multi-port couplers, each having a water inlet, a water outlet, and an ozone input port. The multi-port couplers may simply be pipe/tube fittings with an ozone input port formed therein, 3-way pipe/tube fittings, or the like. Preferably, the multi-port couplers include venturis. A venturi can include an injector venturi design (e.g., a "T" design), where the venturi is coupled between the water inlet and the water outlet, and where ozone is introduced to the venturi through another port (i.e., the ozone input port) positioned perpendicular to the flow path of the water (from the water inlet to the water outlet). During operation, ozone generated by the ozone generators 206 is drawn into the venturi and mixed with the water stream flowing from the water inlet to the water outlet. A pressure differential between the water inlet and the water outlet may serve to facilitate drawing the ozone into the venturi and to facilitate mixing of the ozone and the water. In some embodiments, a pressure differential greater than 20 psi inlet over outlet (e.g., at least a 20 psi difference between the water inlet and the water outlet, with pressure higher at the water inlet) is provided to generate negative suction in the venturi to thereby draw in the generated ozone, while assuring the energy for water flow and pressure for operation of the venturi.

In order to further increase effectiveness of the mixing process delivered by the venturi, the water and ozone solution may pass through an in-line mixer coupled between the venturi and the water outlet. In this regard, each fluid mixer 312 may include a combination of a venture and an in-line mixer. The in-line mixer can facilitate further breaking or mixing of ozone bubbles already introduced to the water to generate a mixture (or solution) of water and substantially uniform-sized ozone bubbles. The small uniform-size ozone bubbles can adhere to each other to lower the surface tension of the water and ozone solution. For example, water can have a surface tension of about 72 Millinewtons, whereas the solution of water and substantially uniform-sized ozone bubbles can have a surface tension of about 48-58 Millinewtons. In embodiments, the in-line mixer has an internal diameter that equals an internal diameter of the output port of the venturi to which the in-line mixer is coupled. The same internal diameter can provide an uninterrupted transition of the fluid flowing from the venturi to the in-line mixer, such as to maintain a vortex action or mixing action of the water and the ozone bubbles. The in-line mixer also provides increased contact time between the water and ozone bubbles and can facilitate preparation of uniform ozone bubble size. In some embodiments, the in-line mixer has a length of about two inches downstream from the venturi, which can allow sufficient time for the velocity of the vortex action caused by the pressure differential of the venturi to crush the gaseous bubbles entrained in the solution into uniformed size bubbles. The in-line mixer can also reintroduce undissolved gas back into the solution resulting in increased efficiency as well as reduced off-gas at the point of application. The in-line mixer can include multiple chambers through which the water and ozone solution flows. The size of the chambers can be determined based on the water flow (e.g., throughput), gas mixing, and desired time exposure. In some embodiments, operation of the system 100 produces a water stream at the water outlet having a molar concentration of ozone of at least 20%, or more particularly at least 25%, far surpassing previous systems that have mass gas transfer rates of less than 10%.

Referring again to FIGS. 1A and 1B, the system 100 may further include one or more oxygen concentrators 102 configured to supply oxygen-enriched air to the one or more air intake ports 216 of each ozone supply unit 200. In embodiments, the oxygen concentrators 102 be configured to direct the oxygen-enriched air through the air dryers 214. The oxygen concentrators 102 may also remove moisture from the air. In this regard, the incoming air may undergo two drying stages. The oxygen concentrators 102 may be fluidically coupled to the ozone supply units 200 (e.g., to the air dryers 214 and/or air intake ports 216) by one or more tubes 104 (e.g., flexible tubing, pipes, etc.) for transferring oxygen-enriched air from the oxygen concentrators 102 to the ozone supply units 200. In an embodiment illustrated in FIGS. 1A and 1B, a first oxygen concentrator 102 is fluidically coupled to a first ozone supply unit 200 by one or more tubes 104, and similarly, a second oxygen concentrator 102 is fluidically coupled to a second ozone supply unit 200 by one or more tubes 104.

Figure 1B:
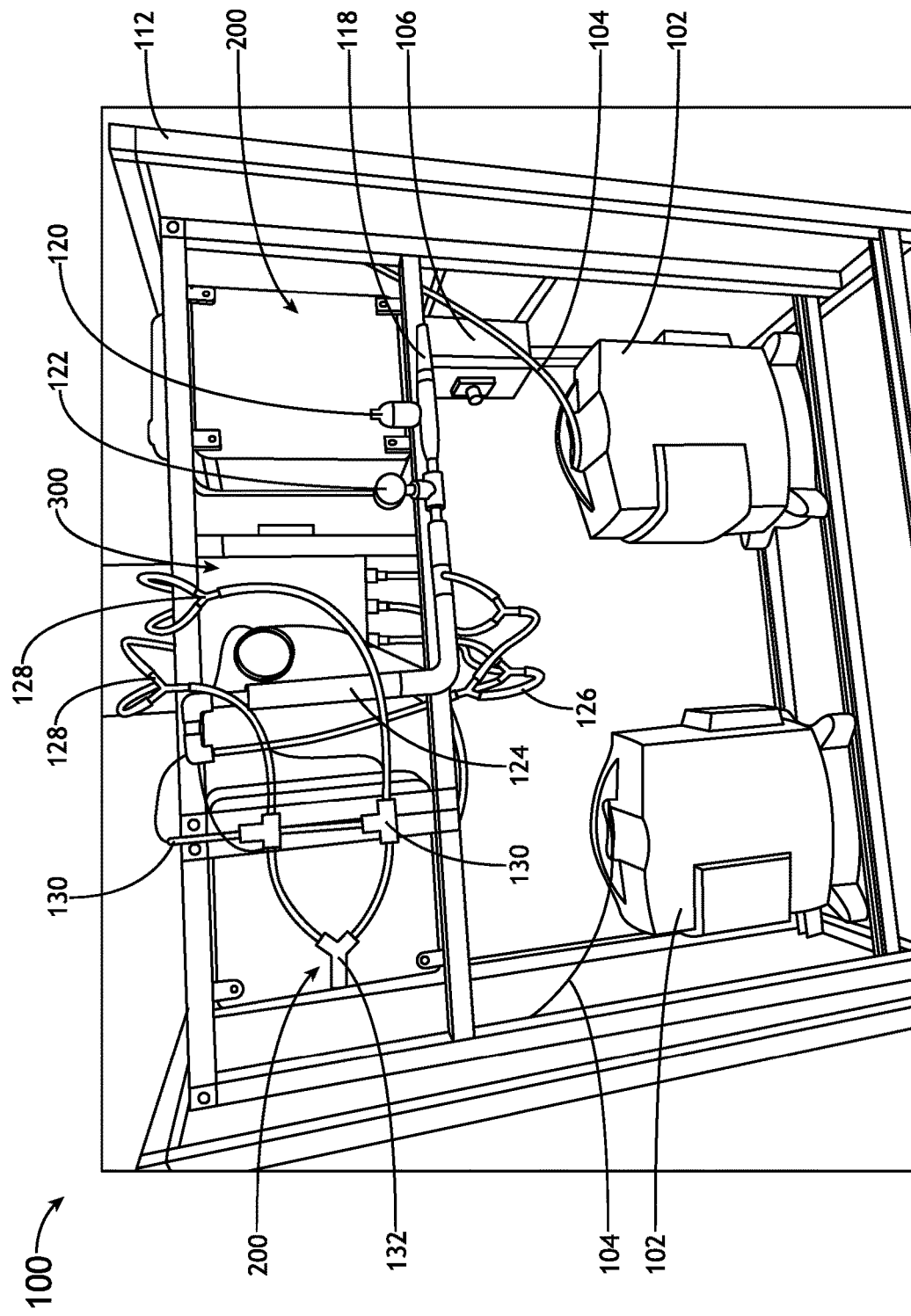
FIG. 1B is a rear view of the system illustrated in FIG. 1A, in accordance with one or more embodiments of this disclosure.

In embodiments, the system 100 may further include one or more ORP monitors 108 configured to detect an ORP of the water flowing through the plurality of fluid paths. For example, as shown in FIG. 1B, the system 100 may include ORP sensors 130 for detecting an ORP of the water and ozone solution dispensed from an outlet 132 of the system 100. In some embodiments, the system 100 may include a first ORP sensor 130 and a first monitor 108 for measuring ORP in a first fluid path 128 associated with a first ozone supply unit 200 and a second ORP sensor 130 and a second monitor 108 for measuring ORP in a second fluid path 128 associated with a second ozone supply unit 200. In this regard, the monitors 108 can be configured to determine operating characteristics of each ozone supply unit 200 so that adjustments can be made if necessary.

The system 100 may include a frame 112 configured to support various components of the system 100 (e.g., the ozone concentrators 102, ozone supply units 200, manifold 300, and various electronics and fluid paths). The frame 112 may be a wheeled frame capable of transporting the system 100 from one place to another. For example, the frame 112 may be supported by a plurality of wheels, casters, or the like. In some embodiments, the system 100 includes a main power switch 106 configured to connect or disconnect power to all of the system components. The main power switch 106 may be mounted to the frame 112. As shown in FIG. 1A, a front side of the frame 112 may also include one or more holsters 110 configured to hold the ORP monitors 108. Referring now to FIG. 1B, a backside of the frame 112 may support fluid paths for connecting the system 100 to an input (e.g., a water source) and an output (e.g., equipment). For example, an input path may include, but is not limited to, a water inlet 118, one or more pressure regulators 120, 122, a pressure gauge 124, and one or more input lines 126 for directing the water into the manifold 300. An output path may include, but is not limited to, one or more output lines 128 for directing water and ozone solution out of manifold 300, one or more ORP sensors 130, and a water outlet 132.

The ozone supply units 200, working together at 5 liters/min each, may be configured to supply ozone to the manifold 300 at a rate of about 10 liters/min. In turn, the system 100 may be configured to dispense water and ozone solution at a rate of about 10 gal/min and can treat water having inlet pressures of between 50 psi and 100 psi to provide water having an ORP of between 600 mV and 1000 mV to provide pathogenic control without introduction of harsh treatment chemicals, such as chlorine. After operation of the system 100, the output water and ozone solution can provide removal of organic and inorganic compounds, can provide removal of micro-pollutants (e.g., pesticides), can provide enhancement of the flocculation/coagulation decantation process, can provide enhanced disinfection while reducing disinfection by-products, can provide odor and taste elimination of the treated water, and so forth. The solubility of ozone in water is quite good, about 10 to 15 times greater than for oxygen under normal drinking water treatment conditions. About 0.1 to 0.6 liters of ozone will dissolve in one liter of water. The size of the ozone gas bubble in the system 100 can influence gas transfer characteristics. In some embodiments, the fluid mixers 312 generate an ozone bubble size of about 2 to about 3 microns. For instance, micro-bubbles can be produced fluid mixers 312 and/or sheared into uniformed micro-size bubbles as the solution passes through the fluid paths.

Corona discharge ozone can be used virtually anywhere, such as with portable versions of the system 100. Since ozone is made on site, as needed and where needed, there is no need to ship, store, handle or dispose of it, nor any containers associated with shipping, storing, handling, and disposing a treatment chemical, as is the situation with most chemicals utilized in water treatment.

The system 100 may be configured to provide indications pertaining to the operation status of the system 100, such as to ensure proper operation, or to provide an indication regarding a need for adjustment, servicing, or maintenance. For example, the flow switches 310 may be configured to send the signal to at least one indicator that provides a visual, tactile, or audible indication that the fluid (e.g., water) is flowing through the fluid paths in the manifold 300. In some embodiments, the indicator is a light source (e.g., an LED) configured to illuminate upon receiving a signal from the flow switches. The indicator may also be coupled to a sensor (e.g., a relay) configured to measure that a voltage is applied to an ozone generator 206. When a proper voltage is applied to the ozone generator 206, the sensor can send a signal to the indicator. In some embodiments, the indicator will provide a visual, tactile, or audible indication when each sensor and the flow switch 310 provide their respective signals to the indicator. For example, the system 100 can include a relay coupled to the power source 212 and the flow switches 310. The relay may be configured to send an activation signal to the indicator when the power source 212 is providing power to the ozone generators 206 and when the flow switches 310 provide signals regarding fluid flow through the system 100. In such a configuration, the indicator can verify that the system 100 is operating under design conditions (e.g., having an active flow of water, and having a sufficient power supply to the ozone generators 206).

In some embodiments, the system 100 may include an in-line ORP meter positioned to measure the ORP of the water and ozone solution, such as adjacent a water outlet, coupled within a distribution line, or the like. The in-line ORP meter can be coupled with the relay 210, such that the in-line ORP meter provides a signal to the relay 210 upon detection of a desired ORP or range of ORPs (e.g., at least 600 mV, at least 650 mV, etc.). The relay 210 can then provide an activation signal to an indicator upon proper functioning of the system 100 (e.g., when the power source 212 is providing power to the ozone generators 206, when the flow switches 310 provide signals regarding fluid flow through the system 100, and when the in-line ORP meter detects a desired ORP of the water and ozone solution generated by the system 100). When the indicator is not activated, this can provide an indication that a component or components of the system 100 may need adjustment, servicing, or maintenance. Alternatively, the system 100 can be configured to activate an indicator upon failure of one or more of the components of the system 100 (e.g., no power supplied to the ozone generators 206, no flow of water detected by the flow switches 310, or an out-of-range ORP detected by the in-line ORP meter).

By providing an ORP of between 600 mV and 1000 mV with the system, the output water and ozone solution can be utilized to destroy various pathogens, including, but not limited to, algae (e.g., blue-green), bacteria (e.g., *Aeromonas* & Actinomycetes, *Bacillus*, Campylobacters, *Clostridium botulinum*, *Escherichia coli* (*E. coli*), *Flavobacterium*, *Helicobacter* (*pylori*), Heterotrophic Bacteria, *Legionella pneumophila*, *Micrococcus*, *Mycobacterium tuberculosis*, *Pseudomonas aeruginosa*, *Salmonella*, *Shigella* shigellosis (dysentery), *Staphylococcus* sp, *albus*, *aureus*, *Streptococcus*, *Vibrio*: *alginolyticus*, anguillarium, *parahemolyticus*, *Yersinia enterocolitica*), fungi, molds, yeasts, mold spores, nematodes, protozoa (e.g., *Acanthamoeba* & *Naegleria*, Amoeboe Trophozoites, *Cryptosporidium*, *Cyclospora*, Entamobea (*histolytica*), *Giardia lamblia*, *Giardia muris*, Microsporidium, *N. gruberi*), trematodes, viruses (e.g., Adenovirus, Astrovirus, Cailcivirus, Echovirus, Encephalomyocarditis, Enterovirus, coxsachie, poliovirus, Hepatitis A, B and C, Myxovirus influenza, Norwalk, Picobirnavirus, Reovirus, Rotavirus).

The water in the water and ozone solution may have a surface tension of about 72 Millinewtons per meter at 20° C. as it enters the system. The system 100 may be configured to reduce the surface tension of the water in the water and ozone solution to about 48-58 Millinewtons per meter at 20° C. The reduced surface tension of the water enables the water and ozone solution being sprayed onto the hard surfaces and equipment to remove grease more effectively from hard surfaces and equipment since ozonated fluid is more capable of loosening and disintegrating any biofilm on the hard surfaces or equipment. The reduced surface tension of the water in the water and ozone solution better enables the cleansing of the hard surfaces and equipment since it more easily penetrates foreign material on the hard surfaces and equipment.

In some implementations, the system 100 may be used for water treatment or decontamination as described below.

Microbiological organisms/species can reside in water sources, including water intended for drinking recreation. Among the microbiological threats is the protozoan parasite—*cryptosporidium* (crypto). Crypto can be a particular challenge for the water treatment industry, however, ozone can eliminate it. Ozone, molecularly known as $O_3$, is a sanitizer and is relentless in its attack of organic microbes (bacteria, viruses, cysts, etc.). Through a process known as lysing, ozone breaks down cell walls or membranes, where it can then destroy the nucleus of the microbe. In addition to sanitation, ozone can provide for the oxidizing of inorganic material that could be present in water, such as metals (e.g., iron and manganese). Although there are a few stronger oxidizers, ozone is the strongest that is readily available for commercial or residential use. For example, ozone is about 1.5 times stronger than chlorine, and can provide a faster oxidizing action. Furthermore, because of this higher oxidation strength, ozone does not build up a tolerance to microbes unlike other sanitizers, such as chlorine. Within the microbial world protozoa, such as crypto, are some of the most resistant to all types of disinfectants. One reason for this resistance is due to its hard outer protective shell, which must be broken through prior to the microbe being inactivated. Crypto can cause a variety of ailments, including abdominal cramping, diarrhea, fever and nausea that can last as long as a month, according to the Centers for Disease Control and Prevention (CDC). Disinfectants used to ward off *cryptosporidium* for water treatment applications can include chlorine (liquid state), chloramines, chlorine-dioxide (gaseous state), and ozone. However, their ability to perform this inactivation duty should not be regarded equal, as each sanitizer requires a specific level of concentration and contact time to take effect, as described by the following.

To better determine the specific amount of the disinfectant required to inactivate or destroy a microbe, the Environmental Protection Agency (EPA) has determined Ct Values. These Ct Values are the product of the disinfectant's concentration (C, expressed in mg/L) and the contact time (t, expressed in minutes). These Ct Values are calculated specifically to the percentage of microbial kill or better known as the log reduction, e.g., 1-Log=90.0 percent, 2-Log=99.0 percent or 3-Log=99.9 percent inactivation of the particular microbe. According to the EPA, chlorine dioxide would require a Ct of 226, which would correlate to 226 mg/L, at one minute of contact time, at 25° C. to achieve a 3-Log reduction or 99.9 percent inactivation. Although, ozone would only require a Ct of 7.4, correlating to 7.4 mg/L, to achieve the same 99.9 percent inactivation with the same parameters as chlorine dioxide. Ct is a product of concentration and time, and as such, both can be manipulated, as long as the given Ct Value is obtained for the desired log reduction (e.g., Ozone Ct of 7.4 can be achieved with a concentration 3.7 mg/L for two minutes of time).

*Cryptosporidium* outbreaks in public drinking waters and recreational swimming pools are becoming more and more of an evident issue. Unfortunately, forms of chlorine sanitation are not often the best solution, especially for high organic and inorganic contaminant levels, as they will create chlorine oxidation by-products, such as trihalomethanes (THM) and chloramine derivatives. These by-products are the typical cause of (what most associate as being over chlorinated) the chlorine smell in drinking or pool waters, and are the cause of itchy, smelly skin and burning eyes in pool water. Although with a properly sized system, ozone can be used as the primary sanitizing and oxidizing agent, oxidizing the contaminants completely. Using ozone in this manner would then allow chlorine to be used as the secondary residual sanitizer to satisfy regulatory requirements, without the production of chloramines and chlorine's side effects.

Further, ozone can be used to remove iron and manganese from water, forming a precipitate that can be filtered:

$$2Fe^{2+}+O_3+5H_2O \rightarrow 2Fe(OH)_3(s)+O_2+4H^+$$

$$2Mn^{2+}+2O_3+4H_2O \rightarrow 2MN(OH)_2(s)+2O_2+4H^+$$

Ozone will also reduce dissolved hydrogen sulfide in water to sulfurous acid:

$$3O_3 + H_2S \rightarrow 3H_2SO_3 + 3O_2$$

The reactions involved iron, manganese, and hydrogen sulfide can be especially important in the use of ozone-based well water treatment. Further, ozone will also detoxify cyanides by converting the cyanides to cyanates (on the order of 1,000 times less toxic):

$$CN^- + O_3 \rightarrow CNO^- + O_2$$

Ozone will also completely decompose urea, where recent outbreaks of *E-coli* in lettuce have been impacted by urea:

$$(NH_2)_2CO + O_3 \rightarrow N_2 + CO_2 + 2H_2O$$

Ozonated fluids produced by the ozonated fluid dispensing system 100 were analyzed. During the production of the ozonated fluid, oxygen is drawn in through an ambient air dryer with the drying capacity to supply sufficient oxygen at a minus dew point to the generating system, the generating system accumulates excess volume of high-quality gas, which is stalled or held in the chambers, thereby supplying a consistent maximum volume of gas resulting in an ample supply of gas to the injecting system, thereby assuring zero cavitation at the point of gas-liquid interface. The pressure differential created by the fluid mixing paths reduces the size of the bubbles to a uniformed size bubbles with a spherical geometry that are entrained in the water, thereby lowering the surface tension of the processed fluid. This process makes the fluid act like a surfactant and reduces the surface tension from 72 Millinewtons per meter at 20° C. to a tested surface tension of 48-58 Millinewtons equal to 140° F. or 60° C. hot water. At liquid-gas interfaces, surface tension results from the greater attraction of liquid molecules to each other due to cohesion than to the molecules in the gas due to adhesion. The net effect is an inward force at its surface that causes the liquid to behave as if its surface were covered with a stretched elastic membrane. Thus, the surface becomes under tension from the imbalanced forces, which is probably where the term "surface tension" came from. Because of the relatively high attraction of water molecules for each other through a web of hydrogen bonds, water has a higher surface tension (72.8 Millinewtons per meter at 20° C.) compared to that of most other liquids. Surface tension is an important factor in the phenomenon of capillary action.

Figure 4:
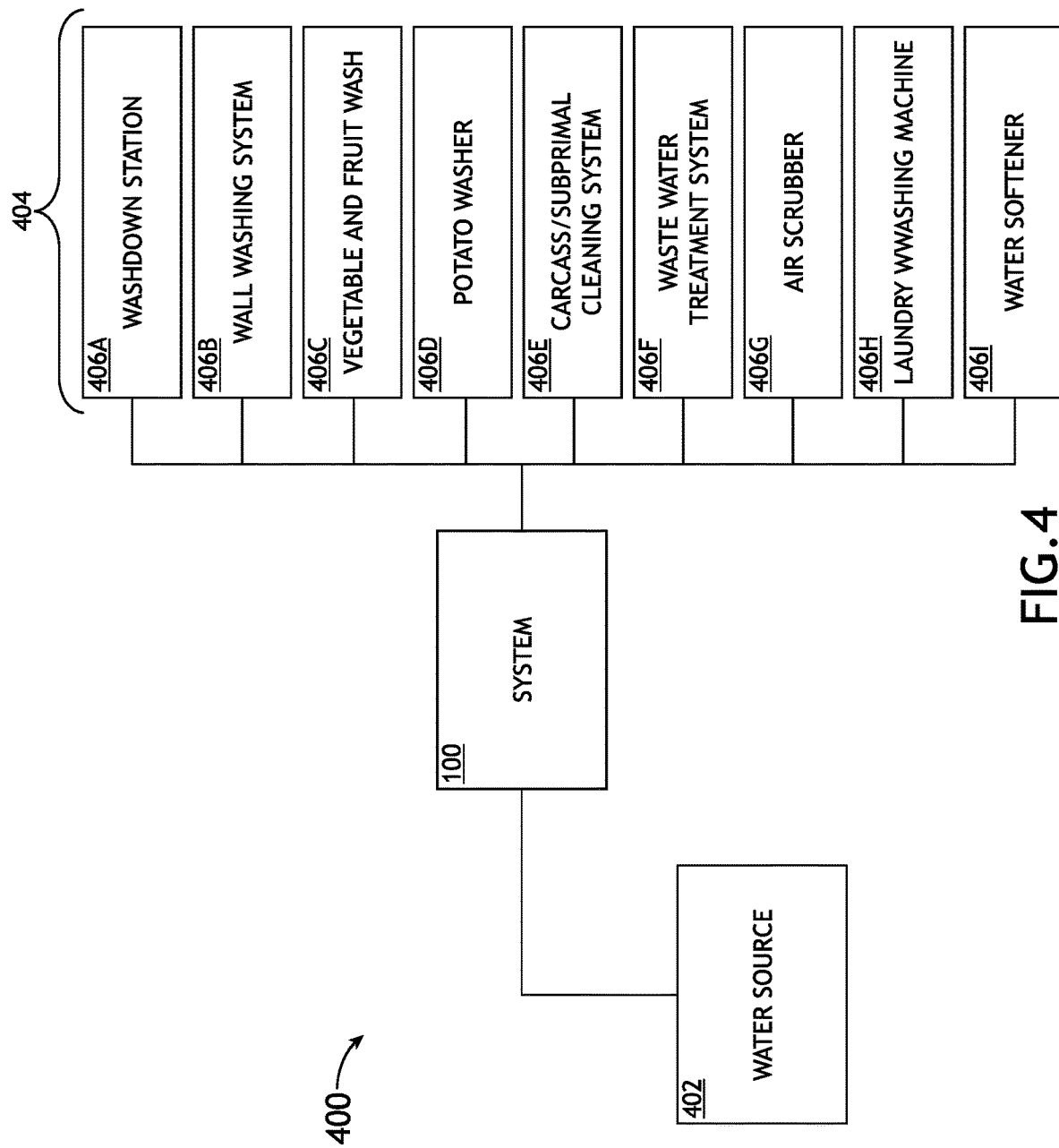
FIG. 4 is a block diagram illustrating one or more applications for the system illustrated in FIGS. 1A and 1B, in accordance with one or more embodiments of this disclosure.

As shown in FIG. 4, the ozonated fluid dispensing system 100 can also be employed within a commercial/industrial system 400 to supply water and ozone solution to one or more commercial/industrial applications for cleansing and/or degreasing purposes. For example, the system 100 may be configured to receive water from a water source 402 (e.g., a conventional water main/supply line, or the like) through water input ports 306, mix the water with ozone, and dispense water and ozone solution from water output ports 308. The system 100 (i.e., water output ports 308) may be used for a single application or a plurality of different applications. For example, in an embodiment illustrated in FIG. 4, the commercial/industrial system 400 include a single supply line or a plurality (e.g., 2, 3, 4, 5, or more) taps 404 that can be used for various equipment. Examples of equipment may include, but are not limited to, washdown stations 406A (e.g., as described in U.S. Pat. No. 10,232, 070), wall washing systems 406B (e.g., as described in U.S. Pat. No. 10,232,071), vegetable and fruit washers 406C (e.g., as described in U.S. Pat. No. 10,238,125), potato washers 406D (e.g., as described in U.S. Pat. No. 10,231, 466), carcass/subprimal cleaning systems 406E (e.g., as described in U.S. Pat. No. 10,834,929), wastewater treatment systems 406F, air scrubbers 406G, laundry washing machines 406H (e.g., as described in U.S. Pat. Nos. 10,233, 583 and 10,233,584), and water softeners 406H. In an example implementation, the system 100 can be used to supply water and ozone solution to a selected piece of equipment, a combination of equipment, or for other equipment not shown in FIG. 4. For example, the system 100 can be used for cleansing and/or degreasing hard surfaces such as plastic, glass, ceramic, porcelain, stainless steel, or the like. The system 100 can also be used for cleansing and/or degreasing equipment such as food service equipment which may include, but are not limited to, ovens, ranges, fryers, grills, steam cookers, oven stacks, refrigerators, coolers, holding cabinets, cold food tables, worktables, ice machines, faucets, beverage dispensing equipment, beer dispensers, shelving food displays, dish washing equipment, and grease traps. The system 100 can also be used for cleansing and/or degreasing HVAC or plumbing systems such as roof top units, air scrubbers, humidifiers, water heaters, pumps, or the like. In general, the system 100 can supply water and ozone solution to any number of taps 404 for any desired purpose.

Figure 5A:
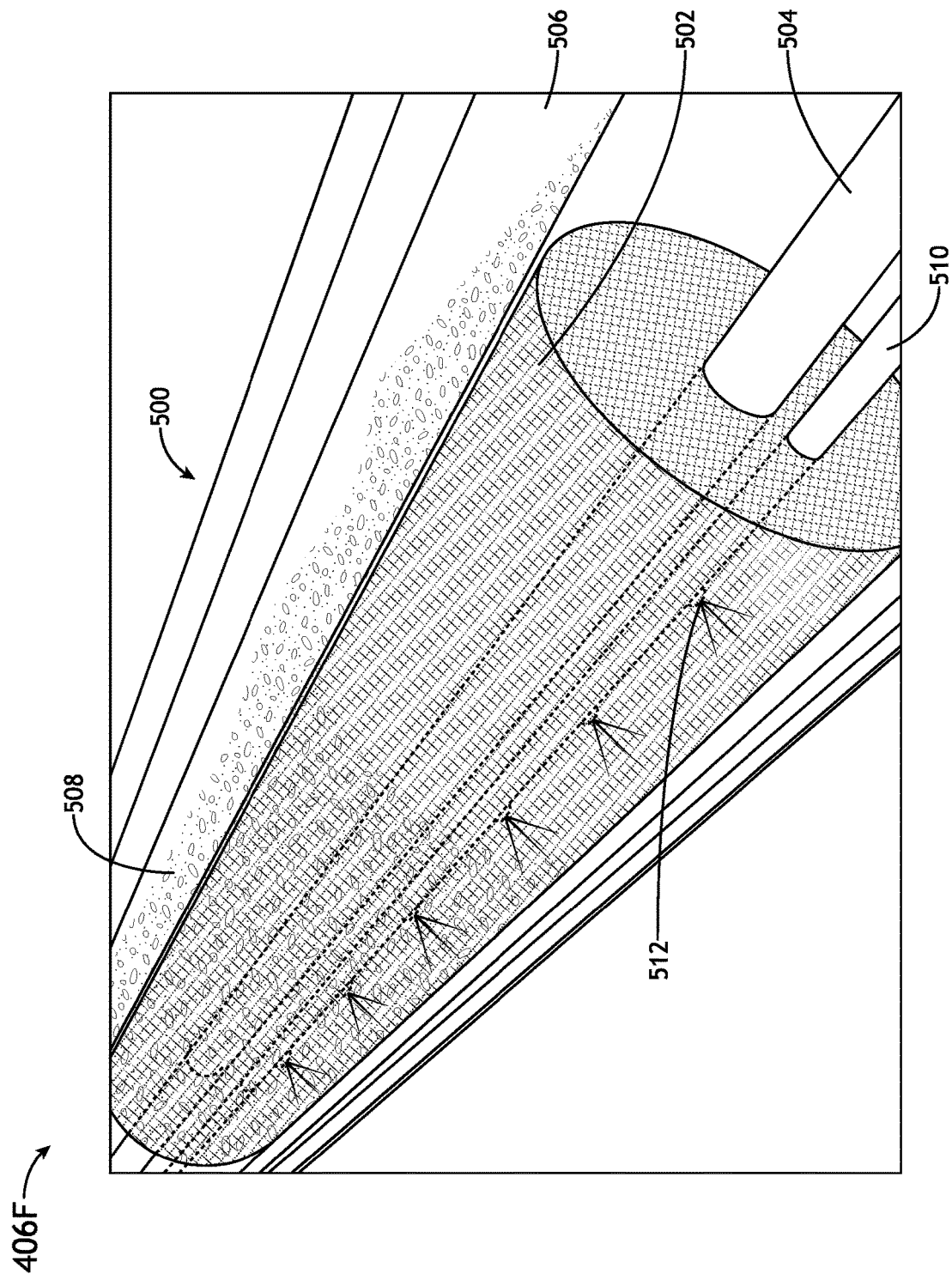
FIG. 5A is a perspective view of a wastewater treatment system that employs the system illustrated in FIGS. 1A and 1B to remove biofilm from a rotating biological contactor using an internal spray bar, in accordance with one or more embodiments of this disclosure.
Figure 5B:
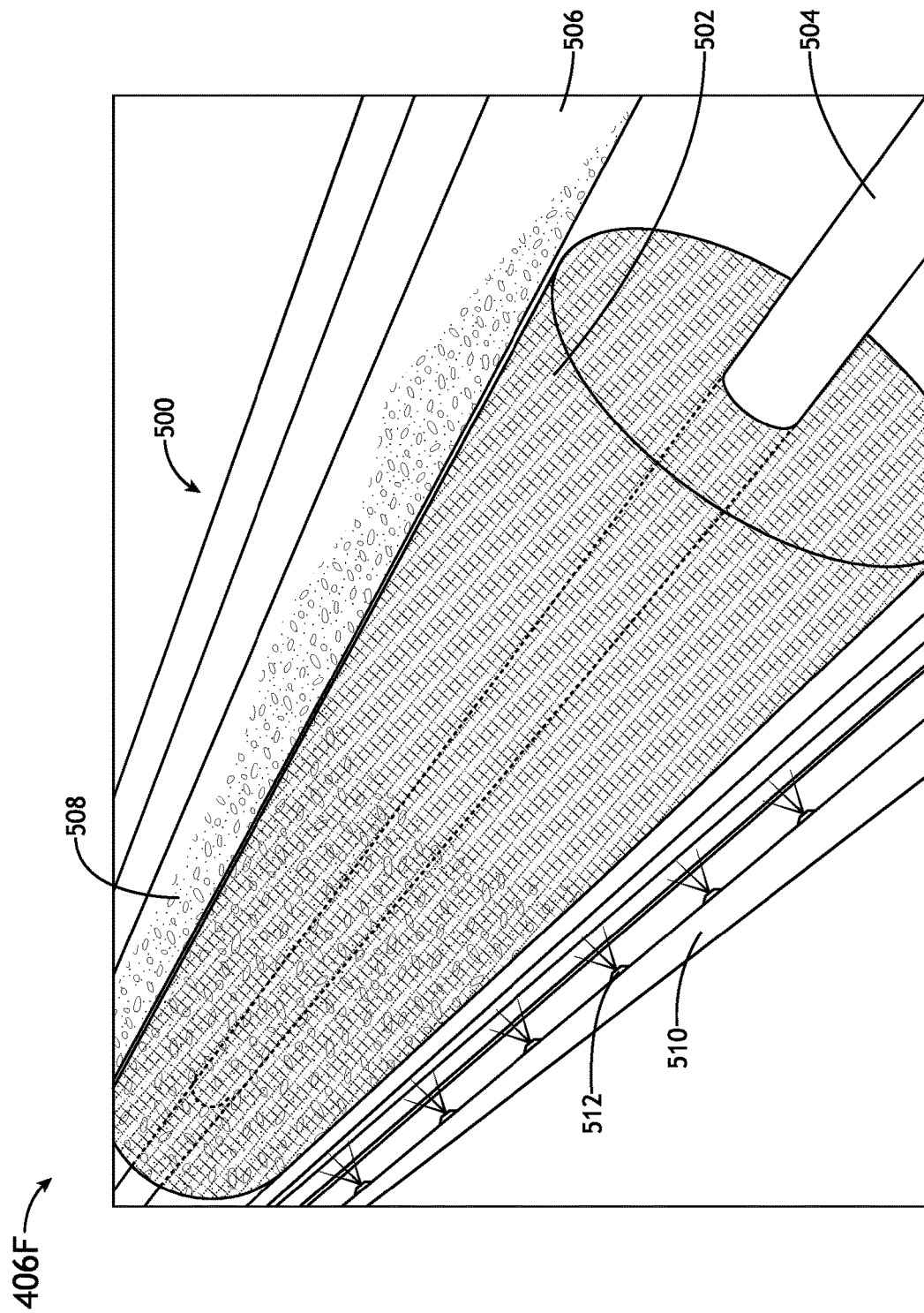
FIG. 5B is a perspective view of a wastewater treatment system that employs the system illustrated in FIGS. 1A and 1B to remove biofilm from a rotating biological contactor using an external spray bar, in accordance with one or more embodiments of this disclosure.

FIGS. 5A and 5B illustrate embodiments of a wastewater treatment system 406F that employs the system 100 to remove biofilm 508 that remains after a disc/drum 502 of a rotating biological contactor 500 rotates against a scraper 506. For example, the system 100 can provide water and ozone solution to a spray bar 510 disposed within the disc/drum 502 (e.g., between a central shaft 504 and an outer surface of the disc/drum 502, as shown in FIG. 5A) or outside the disc/drum 502 (e.g., adjacent to the disc/drum 502, as shown in FIG. 5B). The spray bar 510 includes a plurality of openings/nozzles 512 configured to spray the water and ozone solution at the surface of the disc/drum 502 to loosen and remove the biofilm 508 therefrom. In addition to removing the biofilm 508, the water and ozone solution supplied by system 100 also helps treat (e.g., disinfect and/or soften) the wastewater.

Figure 6A:
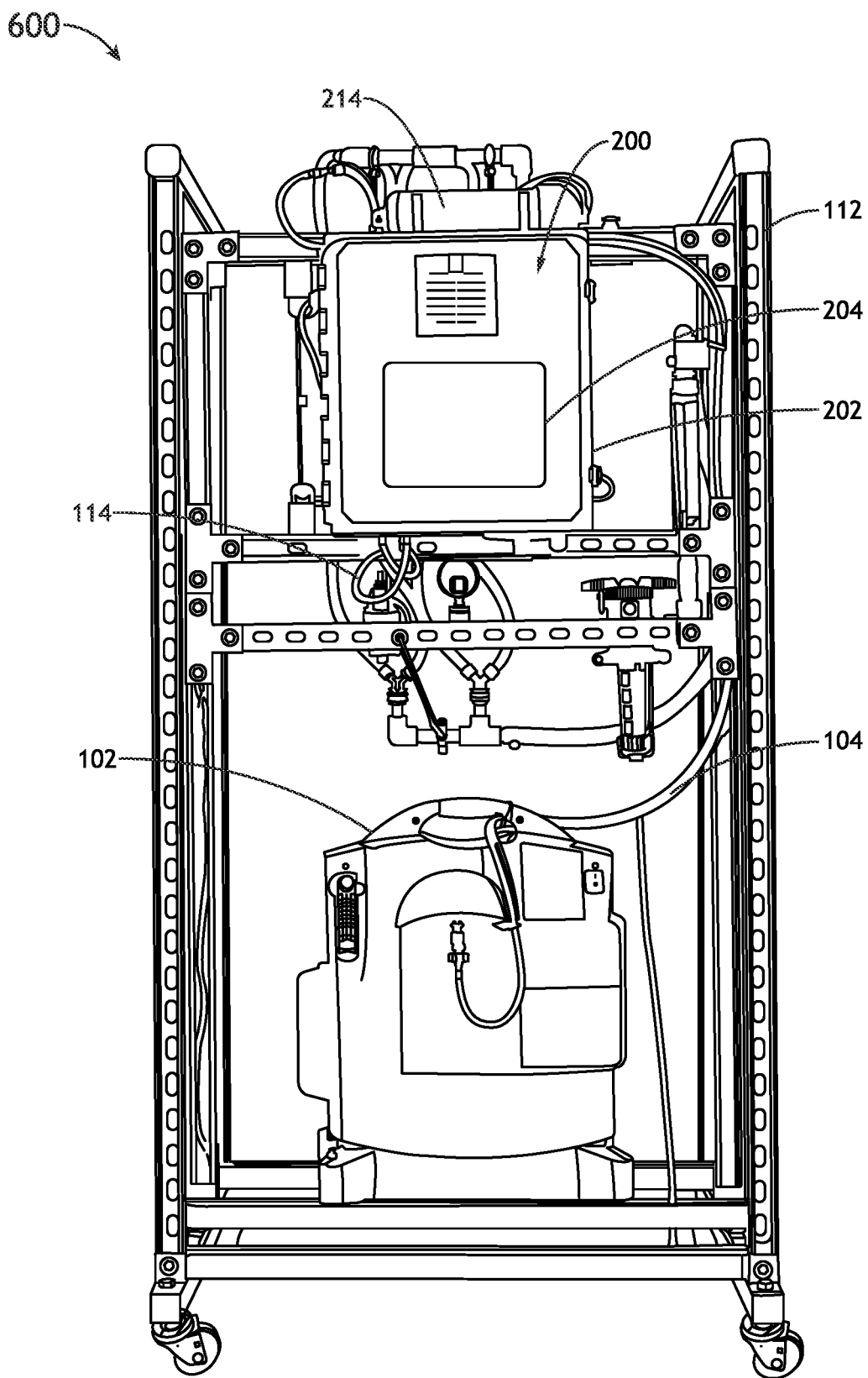
FIG. 6A is a front view of a single-unit system for distributing ozonated fluid, in accordance with one or more embodiments of this disclosure.
Figure 6B:
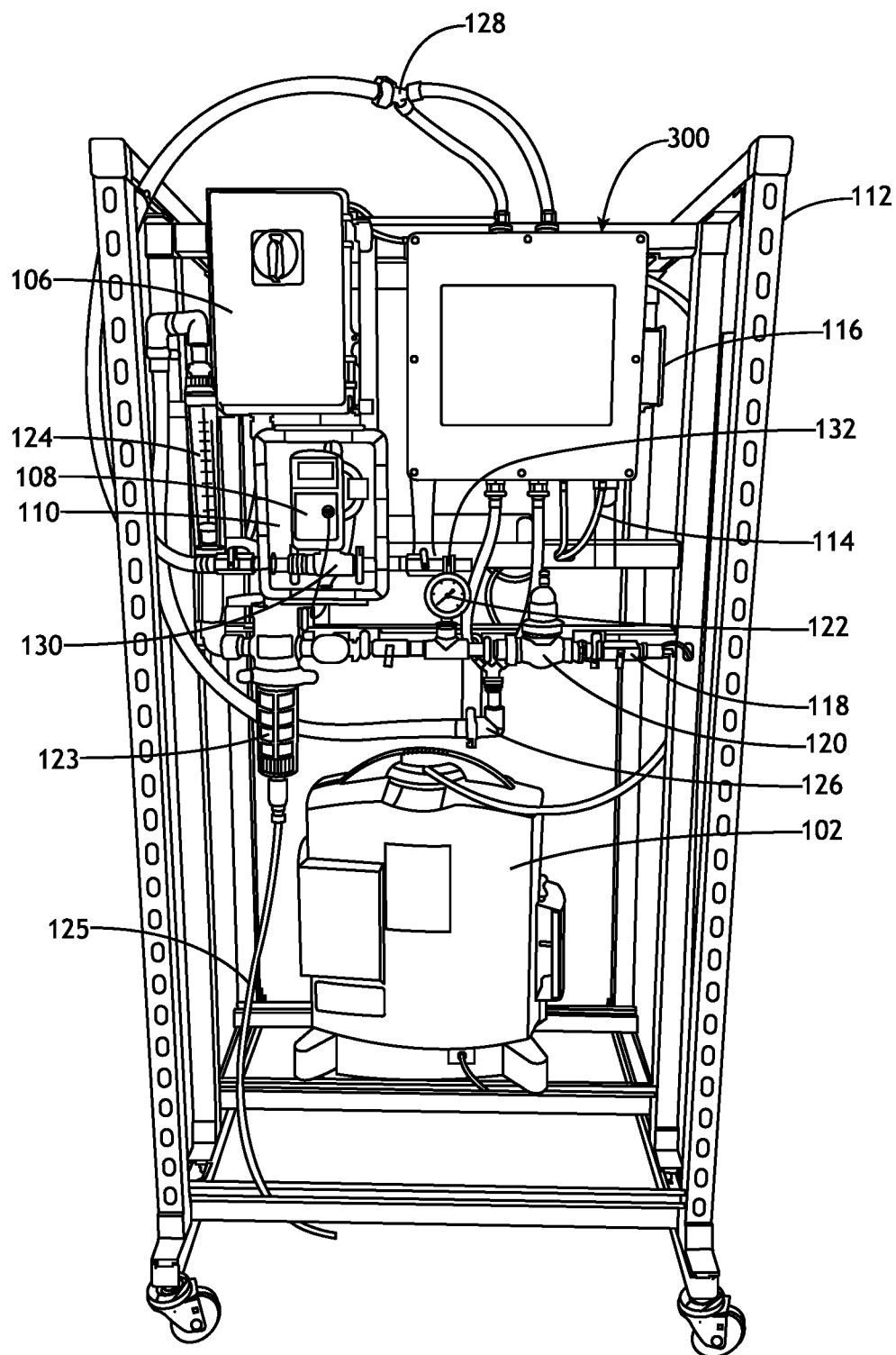
FIG. 6B is a rear view of the system illustrated in FIG. 6A, in accordance with one or more embodiments of this disclosure.
Figure 7:
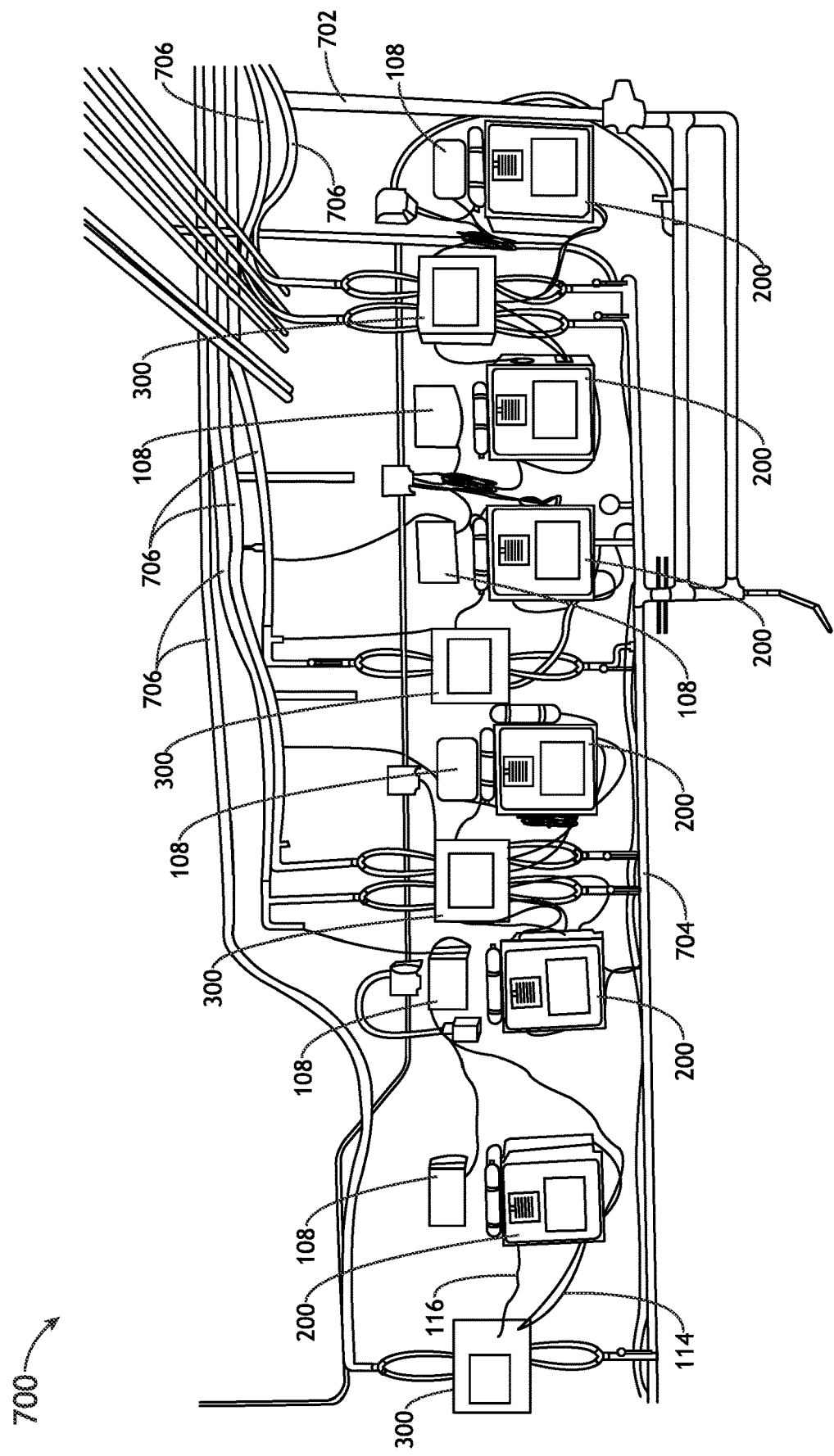
FIG. 7 is a front view of a wall-mounted multi-unit system for distributing ozonated fluid, in accordance with one or more embodiments of this disclosure.

Additional embodiments/implementations of system 100 and/or its components are illustrated in FIGS. 6A through 7.

FIGS. 6A and 6B illustrate a single-unit system 600 that includes a portion of the components of system 100 described above. In this regard, any components (e.g., ozone supply unit 200, manifold 300, etc.) described with reference to system 100 may be identically or similarly structured for system 600. Furthermore, any additional components described with regard to system 600 may be included in system 100 in some embodiments.

In embodiments, the system 600 includes one ozone supply unit 200 configured to output ozone and a manifold 300 to mix the ozone into the water and to distribute a resulting water and ozone solution. Although the system 600 is discussed with regard to applications that employ water to generate a water and ozone solution, it is contemplated that the system 600 may be configured to generate other types of ozonated fluid solutions for the purposes of cleansing, degreasing, decontaminating, and/or fluid treatment.

As shown in FIGS. 6A and 6B, the ozone supply unit 200 and the manifold 300 may include respective enclosures (i.e., supply unit enclosure 202 and manifold enclosure 302). In embodiments, the supply unit enclosure 202 and the manifold enclosure 302 are independently locatable, separate structures. While the supply unit enclosure 202 and the manifold enclosure 302 are separate and capable of being disposed at a distance from one another, the supply unit enclosure 202 and the manifold enclosure 302 are still fluidically coupled by one or more tubes 114 (e.g., flexible tubing, pipes, etc.) for transferring ozone from the ozone supply unit 200 to the manifold 300. The supply unit enclosure 202 and the manifold enclosure 302 may also be communicatively coupled by one or more connectors 116 (e.g., wires, cables, optical fibers, etc.) for transmitting signals between the ozone supply unit 200 and the manifold 300. In other embodiments, the ozone supply unit 200 and the manifold 300 may include wireless communication interfaces (e.g., wireless receivers, transmitters, and/or transceivers) for sending signals from one device to the other.

The supply unit enclosure 202 may have a securable lid/cover 204 that can enclose (e.g., when secured/closed) and provide access to (e.g., when removed/opened) the components housed in an interior portion of the supply unit enclosure 202. In some embodiments, the securable lid/cover 204 may be secured to the supply unit enclosure 202 by a hinge on one side and a latch or fastener on an opposing side. In other embodiments, the securable lid/cover 204 may be a sliding cover or may be secured to the supply unit enclosure 202 by one or more fasteners (e.g., screws to mate with bores in the supply unit enclosure 202, latches, interference fit fasteners, clipping fasteners, magnetic fasteners, or the like). The supply unit enclosure 202 may further include coupling portions to couple with a power source, a switch to engage or disengage power to the ozone supply unit 200/system 600, an indicator (e.g., a light source), any combination thereof, and so forth.

The manifold enclosure 302 may also have a securable lid/cover 304 that can enclose (e.g., when secured/closed) and provide access to (e.g., when removed/opened) the components housed in an interior portion of the manifold enclosure 302. In some embodiments, the securable lid/cover 304 may be a sliding cover or may be secured to the manifold enclosure 302 by one or more fasteners (e.g., screws to mate with bores in the manifold enclosure 302, latches, interference fit fasteners, clipping fasteners, magnetic fasteners, or the like). In other embodiments, the securable lid/cover 304 is secured to the manifold enclosure 302 by a hinge on one side and latch or fastener on an opposing side.

The ozone supply unit 200 and the manifold 300 may be coupled to one another and configured in the same fashion as described above with regard to system 100 and/or with regard to FIGS. 1A through 3. However, the number of paths and connections may differ. For example, in the embodiment illustrated in FIGS. 6A and 6B, the manifold 300 has two fluid paths instead of the four fluid paths illustrated in FIGS. 1A and 1B.

The system 600 may further include an oxygen concentrator 102 configured to supply oxygen-enriched air to the ozone supply unit 200. In embodiments, the oxygen concentrator 102 may be configured to direct the oxygen-enriched air through an air dryer 214 of the ozone supply unit 200. The oxygen concentrator 102 may also remove moisture from the air. In this regard, the incoming air may undergo two drying stages. The oxygen concentrator 102 may be fluidically coupled to the ozone supply unit 200 (e.g., to the air dryer 214 and/or air intake ports) by one or more tubes 104 (e.g., flexible tubing, pipes, etc.) for transferring oxygen-enriched air from the oxygen concentrator 102 to the ozone supply unit 200.

The system 100 may include a frame 112 configured to support various components of the system 100 (e.g., the ozone concentrators 102, ozone supply unit 200, manifold 300, and various electronics and fluid paths). The frame 112 may be a wheeled frame capable of transporting the system 100 from one place to another. For example, the frame 112 may be supported by a plurality of wheels, casters, or the like. In some embodiments, the ozone supply unit 200 mounted to the frontside of the frame 112, and the manifold 300 is mounted to the backside of the frame 112.

In some embodiments, the system 100 includes a main power switch 106 configured to connect or disconnect power to all of the system components. The main power switch 106 may be mounted to the frame 112. For example, the main power switch 106 may be mounted to the backside of the frame 112, as shown in FIG. 6B. The backside of the frame 112 may also include a holster 110 configured to hold an ORP monitor 108. The backside of the frame 112 may support fluid paths for connecting the system 100 to an input (e.g., a water source) and an output (e.g., equipment). For example, an input path may include, but is not limited to, a water inlet 118, one or more pressure regulators 120, 122, a pressure gauge 124, and one or more input lines 126 for directing the water into the manifold 300. In embodiments, the input path may further include a sediment filter 123 configured to remove solids from the input water. In some embodiments, the sediment filter 123 may be configured to dispose of the solids through a waste tube 125. An output path may include, but is not limited to, one or more output lines 128 for directing water and ozone solution out of manifold 300, one or more ORP sensors 130, and a water outlet 132.

The structural arrangement of the system 600 shown in FIGS. 6A and 6B provides a compact system that is easily transported to an application site. The ozone supply unit 200 may be configured to supply ozone to the manifold 300 at a rate of about 5 liters/min. In turn, the system 600 may be configured to dispense water and ozone solution at a rate of about 5 gal/min and can treat water having inlet pressures of between 50 psi and 100 psi to provide water having an ORP of between 600 mV and 1000 mV to provide pathogenic control without introduction of harsh treatment chemicals, such as chlorine.

System 600 may be employed within a system identical or similar to system 400. For example, in the system 400 illustrated in FIG. 4, system 600 may be used in place of system 100.

FIG. 7 illustrates wall-mounted multi-unit system 700 that includes a portion of the components of system 100 described above. In this regard, any components (e.g., ozone supply unit 200, manifold 300, etc.) described with reference to system 100 may be identically or similarly structured for system 700. Furthermore, any additional components described with regard to system 700 may be included in system 100 in some embodiments.

In embodiments, the system 700 includes a plurality of ozone supply units 200 (e.g., two or more ozone supply units 200) configured to output ozone and a plurality of manifolds 300 to mix the ozone into the water and to distribute a resulting water and ozone solution. Although the system 700 is discussed with regard to applications that employ water to generate a water and ozone solution, it is contemplated that the system 700 may be configured to generate other types of ozonated fluid solutions for the purposes of cleansing, degreasing, decontaminating, and/or fluid treatment.

The ozone supply units 200 and the manifolds 300 may include respective enclosures. In embodiments, the supply unit enclosures and the manifold enclosures are independently locatable, separate structures. While the supply unit enclosures and the manifold enclosures are separate and capable of being disposed at a distance from one another, the supply unit enclosures and the manifold enclosure are still fluidically coupled by one or more tubes 114 (e.g., flexible tubing, pipes, etc.) for transferring ozone from the ozone supply units 200 to the manifolds 300. The supply unit enclosures and the manifold enclosures may also be communicatively coupled by connectors 116 (e.g., wires, cables, optical fibers, etc.) for transmitting signals between the ozone supply units 200 and the manifolds 300. In other embodiments, the ozone supply units 200 and the manifolds 300 may include wireless communication interfaces (e.g., wireless receivers, transmitters, and/or transceivers) for sending signals from one device to the other.

Each supply unit enclosure may have a securable lid/cover that can enclose (e.g., when secured/closed) and provide access to (e.g., when removed/opened) the components housed in an interior portion of the supply unit enclosure. In some embodiments, the securable lid/cover may be secured to the supply unit enclosure by a hinge on one side and a latch or fastener on an opposing side. In other embodiments, the securable lid/cover may be a sliding cover or may be secured to the supply unit enclosure by one or more fasteners (e.g., screws to mate with bores in the supply unit enclosure, latches, interference fit fasteners, clipping fasteners, magnetic fasteners, or the like). Each supply unit enclosure may further include coupling portions to couple with a power source, a switch to engage or disengage power to the ozone supply unit 200/system 700, an indicator (e.g., a light source), any combination thereof, and so forth.

Each manifold enclosure may also have a securable lid/cover that can enclose (e.g., when secured/closed) and provide access to (e.g., when removed/opened) the components housed in an interior portion of the manifold enclosure. In some embodiments, the securable lid/cover may be a sliding cover or may be secured to the manifold enclosure by one or more fasteners (e.g., screws to mate with bores in the manifold enclosure, latches, interference fit fasteners, clipping fasteners, magnetic fasteners, or the like). In other embodiments, the securable lid/cover is secured to the manifold enclosure by a hinge on one side and latch or fastener on an opposing side.

One or more ozone supply units 200 may be coupled to each of the manifolds 300 in the same fashion as described above with regard to system 100 and/or with regard to FIGS. 1A through 3. However, the number of paths and connections may differ. For example, in the embodiment illustrated in FIG. 7 (from left to right): a first manifold 300 has two fluid paths and is coupled to one (first) ozone supply unit 200; a second manifold 300 has four fluid paths and is coupled to two (second and third) ozone supply units 200; a fourth manifold has one fluid path and is coupled to one (fourth) ozone supply unit 200; and a fifth manifold 300 has four fluid paths and is coupled to two (fifth and sixth) ozone supply units 200.

Each manifold 300 with one or more connected ozone supply units 200 defines a subsystem that can operate much like system 100 or system 600 described above. The subsystems are configured to output ozonated water to a plurality of ozonated water supply lines 706. For example, each subsystem may be configured to direct ozonated water into at least one respective ozonated water supply line 706 of the plurality of ozonated water supply lines. In some embodiments, the manifolds 300 are configured to output ozonated water to a number of ozonated water supply lines 706 that corresponds to the number of ozone supply units 200. For example, each manifold 300 may be configured to output ozonated water to one ozonated water supply line 706 per connected ozone supply unit 200 (e.g., as shown in FIG. 7).

In other embodiments, each manifold 300 is configured to output ozonated water to one ozonated water supply line 706.

The ozonated water supply lines 706 may be configured to direct ozonated water to separate zones or separate applications. In other embodiments, the ozonated water supply lines 706 are combined and configured to direct ozonated water to a common zone or application. In this regard, system 700 or any of its subsystems may be employed within a system identical or similar to system 400. For example, in the system 400 illustrated in FIG. 4, system 700 may be used in place of system 100.

In system 700, the ozone supply units 200 and the manifolds 300 are wall-mounted and integrated within a water system for a building. In embodiments, the manifolds 300 are configured to receive water from a shared water source 702 (e.g., main water line). The plurality of subsystems are coupled to the shared water source by water source manifold 704 configured to direct water from the shared water source 702 into the plurality of fluid paths of the manifolds 300 of each subsystem.

The system 700 may further include one or more oxygen concentrators configured to supply oxygen-enriched air to the ozone supply units 200. In embodiments, the one or more oxygen concentrators may be configured to direct the oxygen-enriched air through an air dryer of each ozone supply unit 200. The one or more oxygen concentrators may also remove moisture from the air. In this regard, the incoming air may undergo two drying stages.

In embodiments, the system 700 may further include one or more ORP monitors 108 configured to detect an ORP of the water flowing through the plurality of fluid paths. For example, the system 700 may include ORP sensors for detecting an ORP of the water and ozone solution dispensed through the ozonated water supply lines 706. In some embodiments, the system 700 includes at least one ORP monitor 108 for each of the subsystems (e.g., for each of the manifolds 300 or for each of the ozone supply units 200). The monitors 108 can be configured to determine operating characteristics of each ozone supply unit 200 or set of ozone supply units 200 in a subsystem so that adjustments can be made if necessary.

In the embodiment of system 700 illustrated in FIG. 7, the ozone supply units 200, working together at 5 liters/min each, may be configured to supply ozone to the manifolds 300 at a rate of about 30 liters/min. In turn, the system 700 may be configured to dispense water and ozone solution at a rate of about 30 gal/min and can treat water having inlet pressures of between 150 psi and 300 psi to provide water having an ORP of between 600 mV and 1000 mV to provide pathogenic control without introduction of harsh treatment chemicals, such as chlorine.

Although the invention has been described with reference to embodiments illustrated in the attached drawings, equivalents or substitutions may be employed without departing from the scope of the invention as recited in the claims. Components illustrated and described herein are examples of devices and components that may be used to implement embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. A multi-unit system for creating an oxidation reduction potential (ORP) in water to simultaneously disinfect or degrease different equipment, comprising:
a plurality of ozone supply unit enclosures, each ozone supply unit enclosure including:
one or more ozone output ports formed through a sidewall of each ozone supply unit enclosure;
a plurality of ozone generators disposed within each ozone supply unit enclosure, the plurality of ozone generators being fluidically coupled to the one or more ozone output ports; and
one or more controllers disposed within the ozone supply unit enclosure, the one or more controllers being communicatively coupled to the plurality of ozone generators;
a manifold enclosure containing a plurality of fluid paths and having one or more ozone intake ports formed through a sidewall of the manifold enclosure, the one or more ozone intake ports of the manifold enclosure being fluidically coupled to the one or more ozone output ports of each ozone supply unit enclosure by one or more tubes for transferring ozone from the one or more ozone output ports of each ozone supply unit enclosure to the one or more ozone intake ports of the manifold enclosure, wherein the ozone supply unit enclosures and the manifold enclosure are independently locatable, separate structures;
a plurality of flow switches disposed within the manifold enclosure, the plurality of flow switches being configured to transmit one or more control signals to the one or more controllers of each ozone supply unit enclosure in response to sensing a flow of water through the plurality of fluid paths in the manifold enclosure, wherein the one or more controllers are configured to activate the plurality of ozone generators in each ozone supply unit enclosure to generate ozone upon receiving the one or more control signals from the plurality of flow switches in response to sensing the flow of water through the plurality of fluid paths in the manifold enclosure, wherein the ozone is then transferred from the ozone generators to the ozone intake ports of the manifold enclosure via the one or more ozone output ports of each ozone supply unit enclosure and the one or more tubes for transferring ozone from the one or more ozone output ports of each ozone supply unit enclosure to the one or more ozone intake ports of the manifold enclosure;
a plurality of fluid mixers disposed within the manifold enclosure, the plurality of fluid mixers being fluidically coupled to the one or more ozone intake ports and configured to mix the ozone received from the plurality of ozone generators via the one or more ozone intake ports of the manifold enclosure into the water flowing through the plurality of fluid paths in the manifold enclosure; and
a plurality of taps coupled to the plurality of fluid paths, the plurality of taps connected to different equipment including at least two of: a washdown station, a wall washing system, a vegetable and fruit wash, a potato washer, a carcass cleaning system, a wastewater treatment system, an air scrubber, or a water softener, the plurality of taps configured to deliver ozone-enriched water output by the plurality of fluid paths to the different equipment to disinfect or degrease the different equipment.

2. The multi-unit system of claim 1, wherein the one or more controllers comprise a plurality of controllers, wherein each of the controllers is communicatively coupled to a respective ozone generator of the plurality of ozone generators.

3. The multi-unit system of claim 1, wherein the manifold enclosure includes an independent input port and an independent output port for each fluid path of the plurality of fluid paths.

4. The multi-unit system of claim 1, wherein each fluid path of the plurality of fluid paths extends linearly from one side of the manifold enclosure to an opposite side of the manifold enclosure.

5. The multi-unit system of claim 1, wherein each of the flow switches is coupled to a respective fluid path of the plurality of fluid paths.

6. The multi-unit system of claim 1, wherein the plurality of fluid mixers comprises a plurality of multi-port couplers, wherein each of the multi-port couplers includes a water inlet, a water outlet, and an ozone input port.

7. The multi-unit system of claim 6, wherein each of the multi-port couplers comprises a venturi.

8. The multi-unit system of claim 1, further comprising:
one or more oxygen concentrators configured to supply oxygen-enriched air to one or more air intake ports of each ozone supply unit enclosure.

9. The multi-unit system of claim 8, wherein each ozone supply unit enclosure further comprises an externally coupled air dryer, the externally coupled air dryer being configured to remove moisture from the oxygen-enriched air before the oxygen-enriched air is supplied to the plurality of ozone generators through the one or more air intake ports.

10. The multi-unit system of claim 1, further comprising:
one or more ORP monitors configured to detect an ORP of the water flowing through the plurality of fluid paths.

* * * * *